United States Patent
Trakhtenberg et al.

(10) Patent No.: US 8,501,269 B2
(45) Date of Patent: Aug. 6, 2013

(54) SENSITIVE MATERIALS FOR GAS SENSING AND METHOD OF MAKING SAME

(75) Inventors: Leonid Israilevich Trakhtenberg, Moscow (RU); Valdimir Fedorovich Gromov, Moscow (RU); Genrikh Nikolaevich Gerasimov, Moscow (RU); Valeriya Isaakovna Rozenberg, Richland, WA (US); Luke Ferguson, Seattle, WA (US)

(73) Assignee: Apollo, Inc., Kennewick, WA (US)

( * ) Notice: Subject to any disclaimer, the term of this patent is extended or adjusted under 35 U.S.C. 154(b) by 890 days.

(21) Appl. No.: 12/505,090

(22) Filed: Jul. 17, 2009

(65) Prior Publication Data

US 2010/0098593 A1   Apr. 22, 2010

Related U.S. Application Data

(60) Provisional application No. 61/105,935, filed on Oct. 16, 2008.

(51) Int. Cl.
*H01L 21/40* (2006.01)
*B05D 5/12* (2006.01)

(52) U.S. Cl.
USPC .......................... 427/126.5; 73/31.06; 438/49

(58) Field of Classification Search
USPC ............. 73/31.05, 31.06; 438/49; 427/126.3
See application file for complete search history.

(56) References Cited

U.S. PATENT DOCUMENTS

| | | | |
|---|---|---|---|
| 4,387,165 A | 6/1983 | Youngblood | |
| 4,458,242 A | 7/1984 | Kusanagi et al. | |
| 4,490,715 A | 12/1984 | Kusanagi et al. | |
| 4,601,914 A | 7/1986 | Barnes et al. | |
| 5,384,154 A | 1/1995 | De Bakker et al. | |
| 5,427,740 A | 6/1995 | Coles et al. | |
| 5,457,333 A | 10/1995 | Fukui | |
| 5,470,756 A | 11/1995 | Coles et al. | |

(Continued)

FOREIGN PATENT DOCUMENTS

JP     57073661     4/1996

OTHER PUBLICATIONS

J. T. McCue and J. Y. Ying, "SnO2-In2O3 nanocomposites as semiconductor gas sensors for CO and NOx detection," Chem. Mater. Feb. 9, 2007, 19, 1009-1015.*

(Continued)

*Primary Examiner* — Lisa M. Caputo
*Assistant Examiner* — Punam Roy
(74) *Attorney, Agent, or Firm* — Sheldon H Parker, Esq.

(57) ABSTRACT

A gas detection device comprising a measuring circuit, said measuring surface comprising a substrate, a resistance heater bonded to said substrate and a coating, said coating comprising $SnO_2$ nanoparticles doped with $In_2O_3$ nanoparticles and Pd oxide, said Pd oxide being formed from a solution of a Pd salt, such as $PdCl_2$. The $SnO_2$ nanocrystals have a specific surface of at least about 50 $m^2/g$, a mean particle size of between about 5 nm and about 20 nm, and the contact points between individual nanoparticles of $SnO_2$ and $In_2O_3$ and the associated Pd oxide are less than about 100 Å. The Pd salt solution is a solution of a palladium chloride in a dilute acid solution, such as HCl. The palladium salt to an oxide of palladium at an elevated temperature, as for example, by calcining said oxide of palladium. The palladium Marked Copy oxide is in the form of a coating on nanoparticles of $SnO_2$ and $In_2O_3$.

42 Claims, 13 Drawing Sheets

U.S. PATENT DOCUMENTS

| | | | |
|---|---|---|---|
| 5,777,207 | A | 7/1998 | Yun et al. |
| 6,200,674 | B1 | 3/2001 | Kumar et al. |
| 6,449,335 | B1 | 9/2002 | Siochi |
| 6,645,624 | B2 | 11/2003 | Wagle-Peterson et al. |
| 6,759,446 | B2 | 7/2004 | Lee et al. |
| 6,813,931 | B2 | 11/2004 | Yadav et al. |
| 6,918,959 | B2 | 7/2005 | Wang et al. |
| 6,940,086 | B2 | 9/2005 | Gole et al. |
| 6,946,089 | B2 | 9/2005 | Mizouchi et al. |
| 7,104,113 | B2 | 9/2006 | Zribi et al. |
| 7,144,553 | B2 | 12/2006 | Lewis et al. |
| 7,180,108 | B2 | 2/2007 | Kawase et al. |
| 7,237,429 | B2 | 7/2007 | Monty et al. |
| 7,287,412 | B2 | 10/2007 | Ng et al. |
| 7,294,417 | B2 | 11/2007 | Ren et al. |
| 7,361,927 | B2 | 4/2008 | Kawase et al. |
| 2004/0105810 | A1 | 6/2004 | Ren et al. |
| 2007/0009415 | A1 | 1/2007 | Faber et al. |
| 2007/0184576 | A1 | 8/2007 | Chang et al. |

OTHER PUBLICATIONS

R. Diaz, J. Arbol, A. Cirera, F. Sanz, F. Piero, A. Cornet, and J. R. Morante, "Electroless addition of catalytic Pd to SnO2 nanopowders," Chem. Mater. 2001, 13, 4362-4366.*

N. Pinna, A. Bonavita, G. Neri, S. Capone, P. Siciliano, M. Niegerberger, "Nonaqueous synthesis of high-purity indium and tin oxide nanocrystals and their application as gas sensors," Sensors, 2004. Proceedings of IEEE, pp. 192-195 vol. 1, Oct. 24-27, 2004.*

P. Gelin and M. Primet, "Complete oxidation of methane at low temperature over noble metal based catalysts: a review," Applied Catalysis B: Environmental 39 (2000) 1-37.*

S.-J. Hong and J.-I. Han, "Effect of low temperature composite catalyst loading (LTC2L) on sensing properties of nano gas sensor," Sensors and Actuatos A 112 (2004) 80-86.*

Y. Li, G. Lu, X. Wu, G. Shi, "Electrochemical fabrication of two-dimensional palladium nanostructures as substrates for surface enhanced raman scattering," American Chemical Society (Nov. 11, 2006) 24585-24592.*

A. Dieguez, A. Romano-Rodriguez, J. R. Morante, U. Weimar, M. Schweizer-Berberich, W. Gopel, "Morphological analysis of nanocrystalline SnO2 for gas sensor applications," Sensors and Actuators B 31 (1996) 1-8.*

P. Siciliano, "Preparation, characterisation and applications of thin films for gas sensors prepared by cheap chemical method," Sensors and Actuators B 70 (2000) 153-164.*

M. Schweizer-Berberich, J. G. Zheng, U. Weimar, W. Gopel, N. Barsan, E. Pentia, A. Tomescu, "The effect of Pt and Pd surface doping on the response of nanocrystalline tin dioxide gas sensors to CO," Sensors and Actuators B 31 (1996) 71-75.*

G. Neri, A. Bonavita, G. Rizzo, S. Galvagno, N. Pinna, M. Niederberger, S. Capone, P. Siciliano, "Towards enhanced performances in gas sensing: SnO2 based nanocrystalline oxides application," Sensors and Actuators B 122 (2007) 564-571.*

G. Neri, et al., Towards enhanced performances in gas sensing: SnO2 based nanocrystalline oxide, ScienceDirect, Mar. 10, 2006, 8 pages, SNB-9494, Sensors and Actuators B xxx (2006) xxx-xxx, sciencedirect.com S.-J. Hong, J.-I. Han, Effect of low temperature composite catalyst loading (LTC2L) on sensing properties of nano gas sensor, ScienceDirect, Jul. 29, 2002, Sensors and Actuators A 112 (2004) 80-86, sciencedirect.com.

* cited by examiner

SENSITIVE MATERIALS FOR GAS SENSING AND METHOD OF MAKING SAME

REFERENCE TO RELATED PATENT APPLICATIONS

This application incorporates by reference patent application, PCT/RU/2006/000473 filed Sep. 6, 2006, as though recited in full and claims the benefit of provisional patent application 61/105,935, Sensitive Materials for Gas Sensing and Method of Making Same, filed Oct. 16, 2008, the disclosure of which is incorporated by reference as though recited in full.

FIELD OF THE INVENTION

The invention relates to formulation and processing of a sensitive film for use in gas sensing, and more particularly to a multi-component mixture which is optimized for film thickness, porosity, specific surface area, and the number of active centers involved in gas sensing (reducing gases, i.e., $H_2$, CO, $CO_2$ and $CH_4$), still more particularly, to a sensor formed from $SnO_2O$, $In_2O_3$ and $PdCl_2$, and to the method of manufacture of the gas sensor active material.

BACKGROUND

There have been numerous examples of instruments and methods for detecting and measuring specific gases present in an atmosphere. For example, microcalorimetric gas sensors, (pellistors) burn combustible gases with the surrounding air on the surface of a small ball or film of catalytically active metal. The catalyst, e.g. Pt, Pd, or Rh is kept at 500-600° C. The heat of combustion in the presence of a gas is balanced by a reduction in electrical heating power. The power consumption serves as the signal indicating a concentration of flammable gases. This type of sensor is the current standard for the detection of explosives in plants, because it shows a higher accuracy and longer-term stability than the less costly oxidic extensor prevailing in-home applications for the same purpose. Examples include those shown in Debeda, H, Rebiere D, Pistre $J_1$ and Menil J 1995 Sensors Actuators B 27 297-300. Electrochemical gas cells ionize the gas molecule at a three phase boundary layer (atmosphere, electrode of a catalytically active material, electrolyte). Some examples of electrode materials are platinum for CO, gold for a $NO_2$, and activated coal for $SO_2$ detection. Examples of these cells are shown in Brailsford A $D_1$ Yussougg M and Logothetis E M 1992 Technical Digest of the 4$^{th}$ Meeting of Chemical Sensors (Tokyo) ed N Yamazoe (Japan Association of Chemical Sensors) p 160.

Mass sensitive piezoelectric sensors detect a weight change of an absorbtive layer by use of a quartz microbalance or a surface acoustic wave substrate. Examples of these devices are described in Lucklum $R_1$ Hauptmann P 2000 Sensors Actuators B 70 30-6.

Field effect transistors (FET) have also been used as gas sensing devices. Typically, in these arrangements, the gate metal is exposed to the surrounding atmosphere and hydrogen or hydrogen containing gases disassociate or decompose on the surface and the protons defuse to the metal/insulator interface and influence the charge in the semiconductor, thereby changing the drain source current. Examples of such arrangements include those described in Tobias $P_1$ Martensson $P_1$ Baranzahi A, Solomonsson P, and Lundstrom I 1998 Sensors Actuators B 47 125-30 and Lampe U, Gerblinger J and Meixner H, 1992 Sensors Actuators B 7 787-94.

A crucial aspect of the preparation of gas sensors is the deposition of the sensing layer on a substrate surface. Known methods for the deposition of this sensing layer include paste/slurry deposition, chemical vapor deposition (CVD), and physical vapor deposition (PVD). The various chemical and physical vapor deposition (CVD or PVD) techniques are mostly standard processes in the semiconductor industry, the liquid deposition techniques are less frequently employed. However, the compatibility of the latter, i.e. screen printing and drop deposition techniques with semiconductor processes have been shown to be feasible.

One example of a gas sensor is shown in U.S. Pat. No. 5,470,756 issued to Coles et al. Nov. 28, 1995. All documents, patents, journal articles, and other materials cited in the present application are hereby incorporated by reference.

As described by Coles, a gas sensitive layer is formed of $SnO_2$ incorporating $BiO_3$ in an amount less than 35%, but sufficient to confer hydrogen sensitivity and selectivity. Coles further contemplates the inclusion of the catalyst selected from the group of metals Ir, Pt, Ag, Ru, Au or Pd. Coles teaches the deposition of these materials on a substrate as a slurry.

SUMMARY OF THE INVENTION

Drawbacks of the prior art methods include slow response and relaxation times, low sensitivity and limited dynamic detection range, signal stability, high manufacturing costs, and difficulty in reproducing consistent results. Accordingly, new materials and methods of fabrication are needed to improve gas sensors. The present invention is directed towards such materials and methods/processes.

The invention relates to formulation and processing of a gas sensitive film, and more particularly to a method comprising a multi-component mixture which is optimization for film thickness, porosity, specific surface area, and the number of active centers involved in gas sensing (reducing gases, i.e., $H_2$, CO, $CH_4$), still more particularly, a mixture of $SnO_2$, $In_2O_3$ and $PdCl_2$ are milled and processed, and mixed with a surfactant and/or blowing agent, to create a paste composition. The method minimizes particle aggregation, and optimizes porosity, while the use of soluble $PdCl_2$ in the process results in a better dispersion of the activator on to the Sn and In nanometal oxide particles which comprise the sensitive film layer. The resultant gas sensitive film has been found to differ from gas sensitive films of $SnO_2$, $In_2O_3$ and PdO that are not form using a solution of $PdCl_2$. While it is likely that a fine Pd oxide coating is formed on the Sn and In oxides, the present invention encompasses $SnO_2$, $In_2O_3$ and PdO gas sensitive materials formed using a solution of a palladium salt such as $PdCl_2$ irrespective of whether the improvements result from the PdO being coated on the nanoparticle oxides of Sn and In, or because of some other mechanism, as for example, an as yet unidentified interaction between the Sn and In oxides and the PdO.

In accordance with an embodiment of the invention, $SnO_2$ nanocrystals are doped with $In_2O_3$ and a chloride of a platinum group metal. The platinum group metal is preferably Pd, but also can include Pt, Ru, Ir, and combinations thereof. The $SnO_2$ nanocrystals have a specific surface of >20 $m^2/g$ (preferably 50 or greater) and a particle size of between about 5 nm and about 20 nm.

In accordance with another embodiment of the invention, a gas detection device is made from gas sensitive materials, individually processed, combined, processed, and then deposited on a substrate with final thermal processing. The gas sensitive material is deposited on a substrate which is configured as a part of a measuring circuit and is in uses the incorporated heater for thermal processing. The processing temperature is critical to the operation of the sensitive layer at its optimum temperature.

Accordingly, one object of the present invention is to provide a gas sensitive material which exhibits a rapid change in conductivity in the presence of reducing gases, including, but not limited to, $H_2$, CO, $CH_4$, and combinations thereof.

In accordance with a broad aspect of the present invention there is provided a gas sensitive material with high efficiency and fast response manufactured from the composition containing chemical-active components (semiconducting metal-oxides, such as $SnO_2$, $In_2O_3$ etc., and an activator, for example, oxides of a platinum group metal), which provide a high rate of the reaction between sensor sensitive layer and analyzed gas, and structure-forming components (surfactant and blowing agent), which provide high porosity of sensor sensitive layer and free access of analyzed gas to active centers of the sensor;

According to another aspect of the present invention, a five component paste is heat processed to activate the surfactant and/or blowing agent, and fix the pores, and a higher temperature is used to remove/degrade the blowing agent and/or surfactant, and complete the reaction of the $PdCl_2$ (or salt of platinum group metal, for example) to a non-particulate oxide coat forming the final sensitive layer In accordance with an embodiment of the present invention a gas sensitive material comprising $SnO_2$ nanocrystals doped with $In_2O_3$, and an oxide of a platinum group metal is provided. Pd, or a combination of Pd with any platinum group metal, including Pd, Pt, Ru, Ir, and combinations thereof.

In accordance with a preferred embodiment of the invention, the Pd is added to the mixture in the form of a chloride salt in an acidic solution.

In accordance with another embodiment of the present invention a gas sensitive material is produced in which the $SnO_2$ nanocrystals have a specific surface of 10-20 $m^2/g$. In accordance with another embodiment of the present invention a gas sensitive material is produced in which $SnO_2$ nanocrystals have a specific surface of at least about >20 $m^2/g$ (preferably 50 or greater)

In another preferred embodiment of the present invention, the gas sensitive material of $SnO_2$ nanocrystals have a mean particle size of between about 5 nm and about 20 nm.

In accordance with another embodiment, the oxide of the platinum group metal comprises between about 2% and about 5% of the weight of the $SnO_2$ nanocrystals and the $In_2O_3$ comprises between about 3% and about 12% of the weight of the $SnO_2$ nanocrystals. More preferred, the oxide of the platinum group metal comprises about 3% of the weight of the $SnO_2$ nanocrystals and the $In_2O_3$ comprises about 6% of the weight of the $SnO_2$ nanocrystals.

In another embodiment of the present invention, an additive is provided in the mixture of $SnO_2$, oxide of the platinum group metal, and $In_2O_3$. It is preferred, that the additive comprises a surfactant, a blowing agent, and combinations thereof. In this embodiment, the surfactant comprises between about 8% to about 20% of the mixture by weight and the blowing agent comprises between about 3% and about 6% of the mixture by weight. Even more preferred, the surfactant comprises about 15% of the mixture by weight and the blowing agent comprises about 5% of the mixture by weight.

BRIEF DESCRIPTION OF THE DRAWINGS

[The following detailed description of the embodiments of the invention will be more readily understood when taken in conjunction with the following drawing, wherein.

DESCRIPTION OF THE EMBODIMENTS OF THE INVENTION

Figure 1:
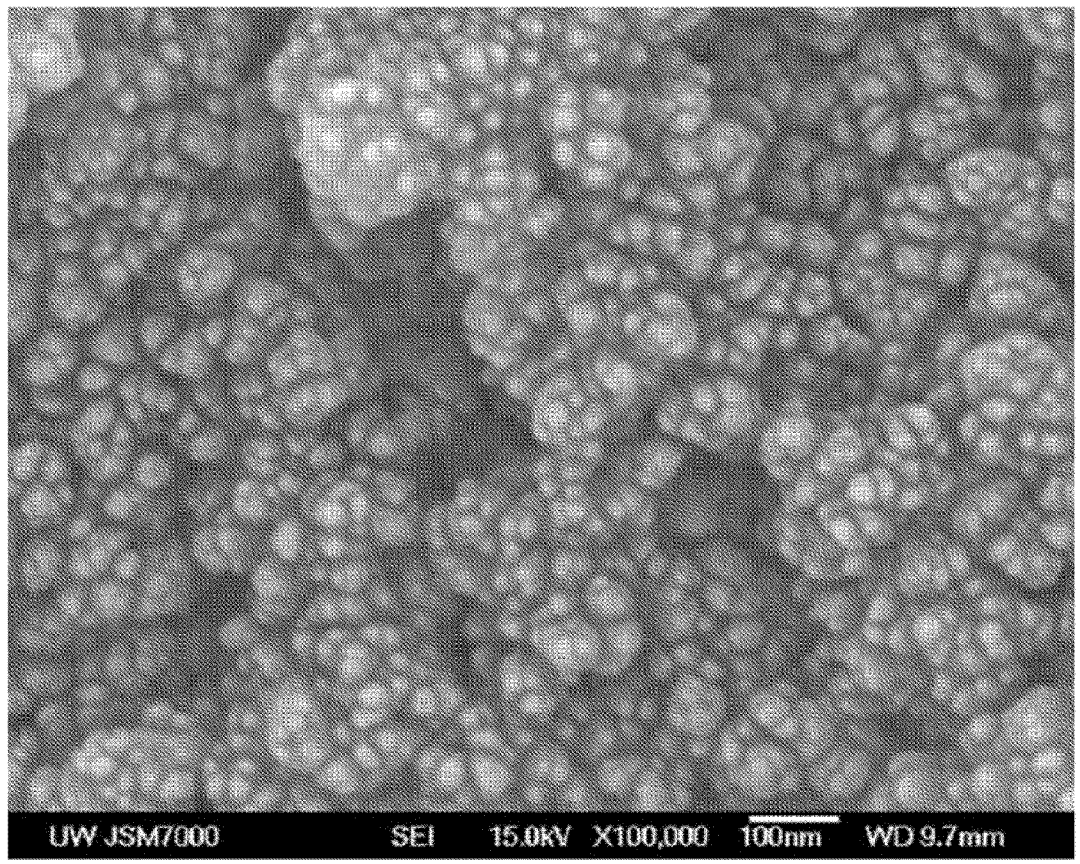
FIG. 1 shows a thick film sensitive layer typical of P (silk screened), 2PG (silk screened), and S1 sensor spray application sensor.
Figure 2:
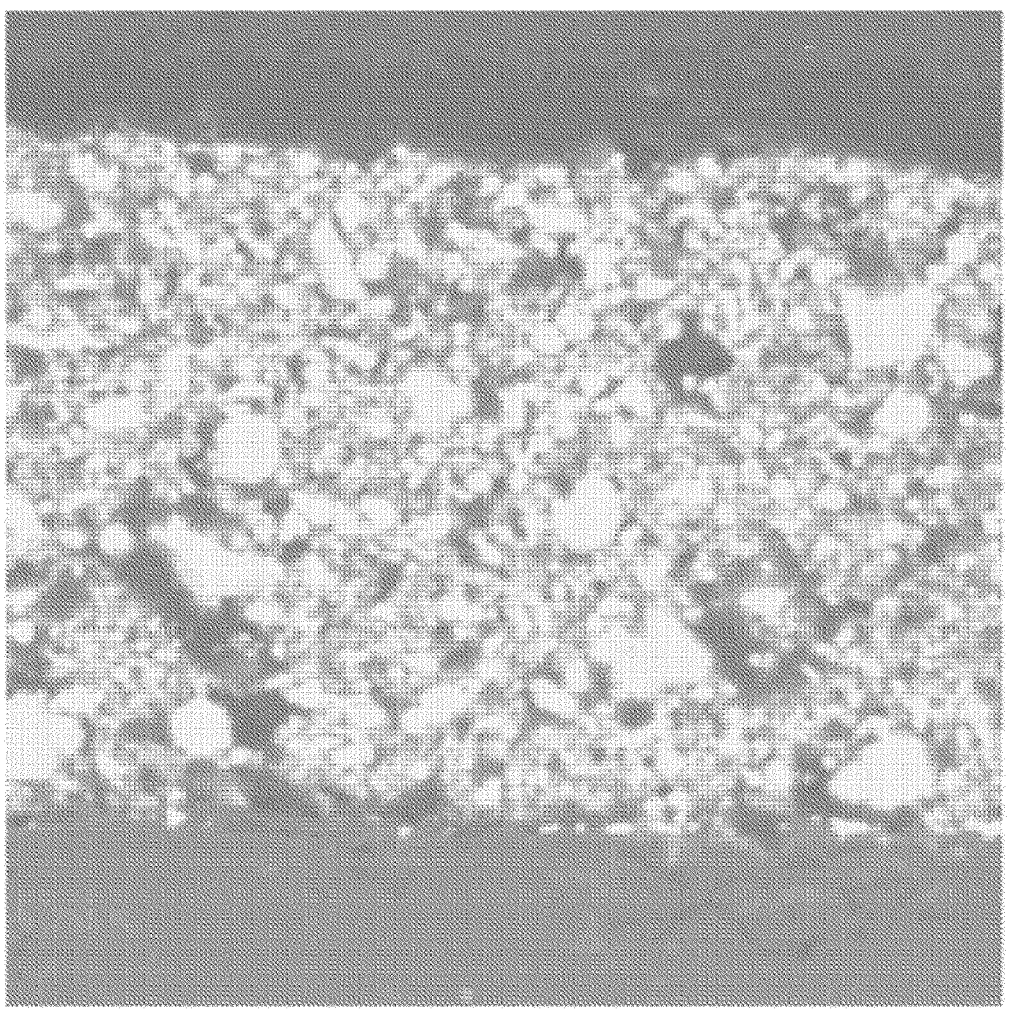
FIG. 2 shows a thick film sensitive layer, typical of A group sensors, where film is applied mechanically.

The invention relates to formulation and processing of a sensitive film, and more particularly to a method comprising a multi-component mixture which is optimization for film thickness, porosity, specific surface area, and the number of active centers involved in gas sensing (reducing gases, i.e., $H_2$, CO, $CO_2$, and $CH_4$). The composition for preparing the gas sensitive material contains chemical-active components (semiconducting metal-oxides and activators, for example, oxides of a platinum group metal), which provide high rate of the reaction between sensor sensitive layer and analyzed gas, and structure-forming components (surfactant and blowing agent), which provide high porosity of sensor sensitive layer and free access of analyzed gas to active centers of the sensors.

A mixture of $SnO_2$, $In_2O_3$ and $PdCl_2$ are milled and processed, and mixed with a surfactant and blowing agent, to create a paste composition. The method minimizes particle aggregation, and optimizes porosity, while the use of soluble $PdCl_2$ in the process results in a better dispersion of the activator, likely as fine Pd oxide coatings onto the Sn and In metaloxide nanoparticles, which comprise the sensitive film layer.

The process and formulation produces gas sensors possessing high sensitivity, good selectivity, signal stability, as well as fast response and relaxation times are especially important for safety sensors, which allow very quickly and precisely detecting the analyzed gas when its concentration is near to critical concentration.

The theoretical approach not only indicates that the two factors work together; this is the chemical activity of the sensitive layer, and ease of access to active centers. It is necessary to emphasize that sensor efficiency of this type, is determined not by the chemical activity of the sensitive layer alone, but the number and access of analyzed gas to the sensor active centers as well. Several factors which control both the number of centers and access to active centers include: film thickness, porosity, particle surface area, and the spatial contact distances that allow for both gas penetration through the pores and interaction, and the required rapid chemistry that enables the sensor to function.

Preferably, the gas sensitive material of $SnO_2$ nanocrystals has a mean particle size of about 5 nm and about 20 nm. Those having ordinary skill in the art will recognize that on occasion incomplete oxidation of the platinum group metal will occur. Accordingly, some fraction of the platinum group metal may be present in the final gas sensitive material in an unoxidized form. Further, operation of a device incorporating the gas sensitive material may cause the reduction of the metal oxide. Thus, it should be understood that the presence of some fraction of the platinum group metal in an unoxidized form in the final gas sensitive material is expressly contemplated herein.

In the conductometric semiconducting metal-oxide sensor such centers are oxygen ions $O^-$ chemisorbed at the metal-oxide surface. The reaction of reducing gas (for example, $H_2$, $CH_4$, CO2, CO, etc.) with such centers results in removing chemisorbed oxygen and releasing electrons, which transfer in sensor conduction bond thus increasing its conductivity. Thus, the sensing effect is characterized by a conductivity rise of the metal-oxide sensitive layer with the addition of reducing gas. In the $H_2$ case this process can be represented by the following, where $e^-$ is a releasing electron, which transfers in the sensor conduction bond.

$$O^- + H_2 \rightarrow H_2O + e^-,$$

Prior patents/references have reported these types of sensor systems based on combinations of $SnO_2$ with a trivalent metal (for example, $In_2O_3$), and oxides of platinum group metal (as, PdO), and have chemical activity in the reactions with reducing gases, and have been used as a sensitive layer in the conductometric sensor. These citations show rather long response times to $H_2$, have a limited dynamic concentration range (<2%), and less than desired selectivity (i.e., CO, $CH_4$, $CO_2$). In addition, sensor longevity is generally less than the 2+ year range required for commercial applications.

It has now been found that dynamic range and faster response times and relaxation times of such sensors can be controlled by diffusional factors associated with the sensitive layer, namely by the hindrances affecting the analyzed gas's access to active centers for the sensing gas. Thus, porosity factors are influenced by film thickness, porosity, particle surface area, and the spatial contact distances, which are presently going to be addressed below.

The sensitive layers of this type of sensor, as a rule, consists of a system of pores and active centers, which allow for sensing of the target gas; this occurs at the active centers, which encompass both larger pores, and the >100 Å pores/spaces between the active center at contact points. This reaction is the basis of the sensing effect. The sensitivity and the response time of the sensor are governed not only by the rate of the reaction but by the diffusion rate of analyzed gas to the active centers of the sensor. As known, the diffusion rate of a gas ($D_K$) into porous structure is determined by Knudsen equation $$D_K = 9700 r \times \sqrt{\frac{T}{M}} \qquad (1)$$

where r=pore radius (cm), T=temperature (K) and M=molecular mass of the gas.

Interaction of analyzed gas with surface active centers of the sensor (oxygen particles) is described by the following equation [1]:

$$\frac{\partial C_A}{\partial t} = D_K \left( \frac{\partial^2 C_A}{\partial x^2} \right) - k C_A \qquad (2)$$

where x=the distance from the film surface, $C_A$=the concentration of analyzed gas at the distance x from the film surface, k=rate constant of the reaction of analyzed gas with surface active centers. In the stationary state, when $C_A$ does not change in the time, eq. (2) becomes:

$$D_K \left( \frac{\partial^2 C_A}{\partial x^2} \right) - k C_A = 0 \qquad (3)$$

The solving of eq. (3) gives the stationary distribution of the gas concentration $C_A$ along the pore length. The dependence of the ratio $C_A/C_{A,s}$ (where $C_{A,s}$=concentration of analyzed gas in the environment at x=0) on x/L (where L=the thickness-porosity of the sensitive layer) is shown in the FIG. 12 at various values of parameter $L(k/D_k)^{1/2}$. Porosity is related to thickness in that the thicker the sensitive layer is, the more porosity that is required to maintain or improve sensor efficiency.

Porosity has two forms. There is the gross porosity which consists of 10 to >100 nm open pores typical of thick film layers and indeed aids diffusion of analyzed gases into the deeper layers of the film. This gross porosity is affected by the blowing agent. In contrast to gross porosity, there is the more important molecular level porosity. This is represented by the <100 Å contact points between the individual nanoparticles of Sn- and In oxide, and the associated Pd oxide. This molecular level porosity accounts for the actual efficacy and number of active centers related to $O_2$, $H_2$, and other reducing gases. In our system this molecular level porosity is controlled by the surfactant which places an angstrom thick coating on the nanoparticles, and the surfactant is removed in the final calcining step, leaving the contact distances necessary to increase the number and efficacy of the active centers.

Figure 12:
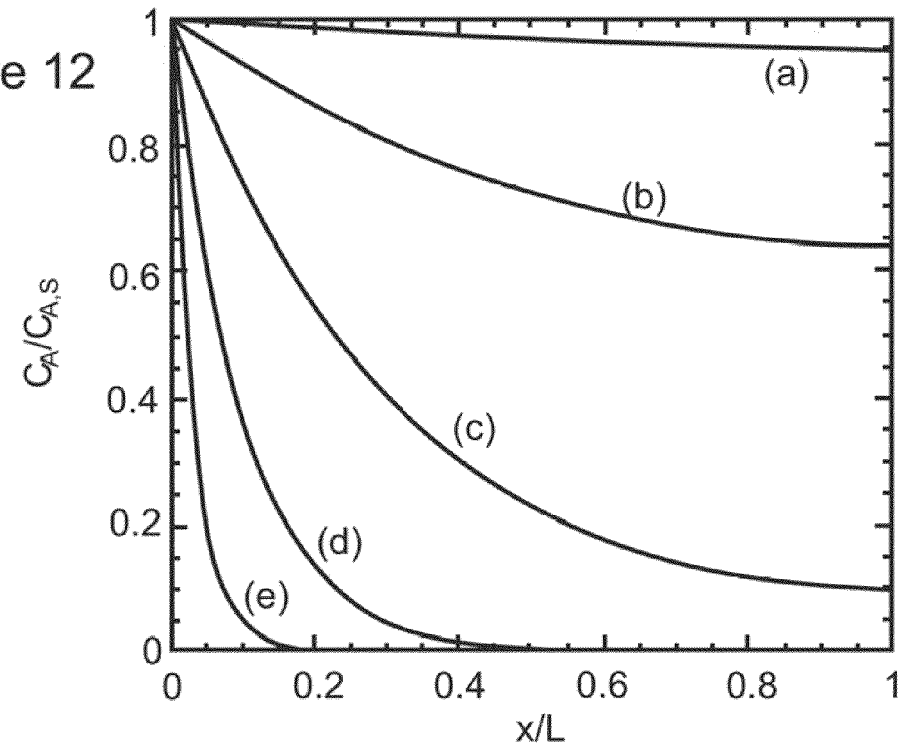
FIG. 12 is a plot of generalized concentration profile.
Figure 13:
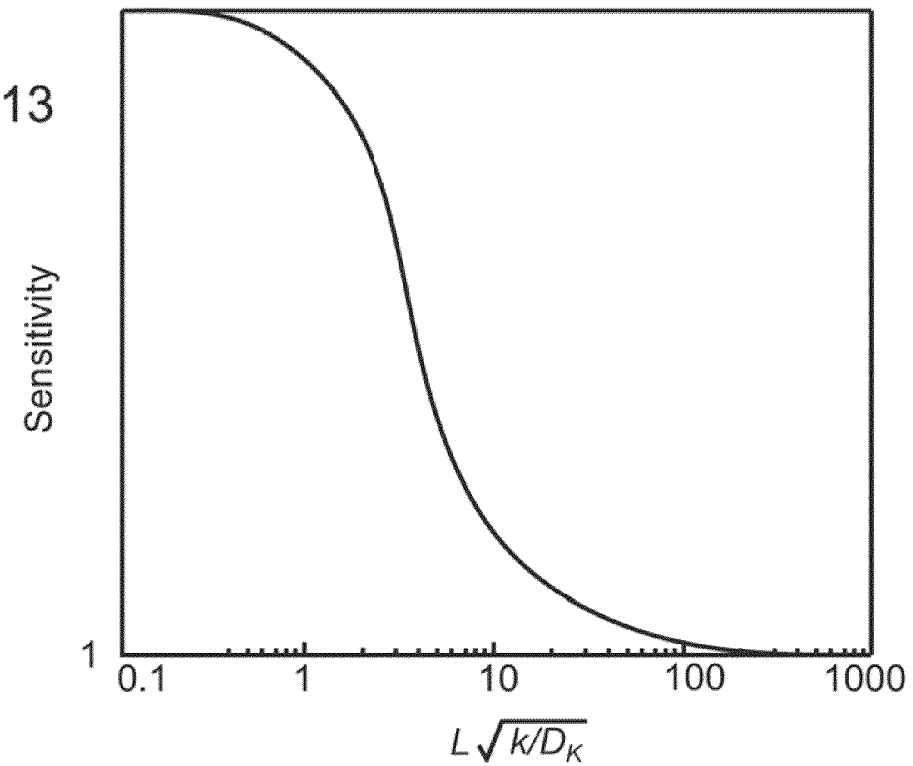
FIG. 13 is a plot of a generalized expression of the gas sensitivity of films at a fixed temperature.

As can be seen from FIG. 12 the decreasing of the parameter $L(k/D_k)^{1/2}$ leads to increasing of the effective working layer of the sensor that is the part of the sensor sensitive layer, where the sensing reaction takes place. Therefore by increasing the gas diffusion coefficient $D_K$ in pores at fixed value of the reaction rate constant k, which is determined by chemical properties of sensor system, we can reach the situation, in which reaction between the active oxygen centers and analyzed gas takes place practically across the whole width/volume of the sensitive layer. In this case the sensor sensitivity rises sharply as well as seen in FIG. 13. As can be seen from equation (2) the rise of $D_K$ leads to increasing the rate of change of the analyzed gas concentration inside the pores, i.e. to decreasing the time of the steady state achievement that is the sensor response time.

Thus, to create gas sensors with high sensitivity, rapid response/relaxation times, and excellent selectivity to $H_2$, a novel method is provided for the preparation of a high-sensitive layer with a structure having a relatively thin film thickness, high porosity, high particle surface area/volume, and optimal spatial contact distances. This improved sensitive layer is comprised of a multi-component pre-application paste, composed of two metal oxide nanoparticles, a surfactant and blowing agent to greatly reduce nanoparticle aggregation and develop film porosity. $PdCl_2$ is employed to effectively coat the Sn- and In oxide nanoparticles with Pd oxide in the preparation procedure.

It should be taken into account that according to equation (1) gas diffusion coefficient $D_K$ in pores rises proportionally to the pore radius "r". To obtain the optimal sensitive layer structure with the above characteristics we produced a novel five component paste composition, containing along with common nanopowder oxides (for example, $SnO_2+In_2O_3$), an activator (such as $PdCl_2/PdO$), a surfactant and a blowing agent. Once the 20-40 nm nanopowder oxides of Sn and In are milled to 5-10 nm, $PdCl_2$ solution is blended in with the nanometal powders to allow the Pd to associate with the oxide nanoparticles, and slowly convert to a dispersed Pd oxide. While the theory behind the procedure is not a limitation of the invention, it can be stated that this is believed that this part of the procedure helps to increasing the number and function of the sensing active centers.

A fundamental feature of this method lies in the fact that the addition of a surfactant (for example, stearic acid) in the paste composition (used for sensitive layer preparation) reduces significantly the interaction between the metal oxide particles (by reducing the aggregation/adhesion of particles at the molecular scale). For this reason the formation of pores (under the action of gases resulting from the early decomposition of the blowing agent (for example, ammonium carbonate) occurs far easier (more effectively) resulting in an increase in number and radius of pores. Thus, there is a synergy in the use of a combination of a surfactant and a blowing agent. Thus, the porous structure of sensitive layer produced by this particular method guarantees free access of analyzed gas to the active centers. While the theory behind the procedure or other aspect of the invention is not a limitation of the invention, it is noted that this synergy may be a main or primary reason why the sensors of the present invention are characterized by a high sensitivity (in the concentration range from 0.001 to >6% $H_2$) and fast response time for the analyzed gas. The achieving of a high sensitivity and fast response time is shown by the fact that the response time of our sensors (for example, about 1 sec. for $H_2$) are consistent with characteristic time of chemical reaction type of sensors. That means that we avoided the diffusion restriction in the typical sensitive layer for this type of sensor. Sensor response to $H_2$ and other gases can be increased from the normal 1-2% seen in other sensors, to 6-10% $H_2$ in our improved sensor, by preparing and processing the formulation/paste in such a way that when the applied paste is processed (heated), the use of a blowing agent and/or surfactant can induce the needed porosity, and the surfactant produces an organic ionic association with the nanoparticle oxides, to leave behind after calcining, sufficient space for the reactive sites to be large enough to accommodate both the $O_2$ and sensed gas, but not too large (>~100 A). Additionally, the thickness of the sensitive layer, its porosity, and thus the number of available reactive sites dictates the actual quantity (concentration) of a sensed gas.

It is thus seen that increased sensitivity at lower $H_2$ concentrations and the dynamic sensing range to a level as high as 10% $H_2$ is achieved by increasing both gross porosity and molecular level porosity. As noted above, this increases the specific surface area, as well as the number of active centers.

By way of emphasis, it is noted that the increase in the number and radius of pores results in a more porous structure of the sensitive layer and improves/guarantees free access of the analyzed gas to sensor active centers. This results in sensors which are characterized by high sensitivity and short/fast response times for the analyzed gas, as would be expected for chemical/electrochemical sensors. It should be especially noted that the response time of our sensors (for example, about 1 sec for $H_2$) points out that we have achieved the removal of the diffusion restriction in this FET type sensor/sensitive layer, resulting in excellent response time with minimal contaminate/poisoning experienced in the chemical detectors.

It should be noted that it has now been found that that strong bond between the metal oxide nanoparticles in the paste composition observed in the absence of surfactant did not allow the creation of a sensor with high porous structure and consequently with fast response time.

In accordance with a preferred method of the present invention, a five component paste is heat processed to activate the blowing agent, and fix the pores. Additionally, a higher temperature than previously employed is used to remove/degrade the blowing agent and surfactant, and complete the reaction of the $PdCl_2$ to an oxide coat forming the final sensitive layer.

The gas sensitive material comprises $SnO_2$ nanocrystals doped with $In_2O_3$, and an oxide of a platinum group metal. While it is preferred that Pd, or a combination of Pd with any of Pt, Ru, Ir, be selected as the platinum group metal, suitable platinum group metals include Pd, Pt, Ru, Ir, and combinations thereof. Preferably, the Pd is added to the mixture in the form of a chloride salt in an acidic solution. Preferably, the $SnO_2$ nanocrystals have a specific surface of 7 $m^2/g$.

A gas sensitive material is produced in which $SnO_2$ nanocrystals have a specific surface of at least about >20 $m^2/g$ (likely 50 to 100). Preferably, the $SnO_2$ nanocrystals have a mean particle size of between about 5 nm and about 20 nm.

Those having ordinary skill in the art will recognize that on occasion incomplete oxidation of the platinum group metal will occur. Accordingly, some fraction of the platinum group metal may be present in the final gas sensitive material in an unoxidized form. Further, operation of a device incorporating the gas sensitive material may cause the reduction of the metal oxide. Thus, it should be understood that the presence of some fraction of the platinum group metal in an unoxidized form in the final gas sensitive material is expressly contemplated herein.

Preferably, the oxide of the platinum group metal comprises between about 2% and about 5% of the weight of the $SnO_2$ nanocrystals and the $In_2O_3$ comprises between about 3% and about 12% of the weight of the $SnO_2$ nanocrystals. More preferred, the oxide of the platinum group metal comprises about 3% of the weight of the $SnO_2$ nanocrystals and the $In_2O_3$ comprises about 6% of the weight of the $SnO_2$ nanocrystals.

Preferably an additive is provided in the mixture of $SnO_2$, oxide of the platinum group metal, and $In_2O_3$. It is preferred, that the additive comprises a surfactant, a blowing agent, and combinations thereof. In this embodiment, the surfactant comprises between about 8% to about 20% of the mixture by weight and the blowing agent comprises between about 3% and about 6% of the mixture by weight. Even more preferred, the surfactant comprises about 15% of the mixture by weight and the blowing agent comprises about 5% of the mixture by weight.

Ammonium carbonate is preferred as a blowing agent. Upon heating, ammonium carbonate decomposes to a gas form, and is thereby removed from the mixture as $CO_2$ and $NH_3$. Other suitable compounds for use as a blowing agent include, but are not limited to, the azo-compounds (which decompose with liberation of $N_2$), and ammonium chloride (which decomposes with formation of $NH_3$ and $HCl$).

Also, stearic acid is the preferred surfactant. As with the blowing agent, the surfactant is also decomposed to gas products and thereby removed from the mixture during the formation of the gas sensitive material. Other suitable surfactants include, but are not limited to, carbonic acids with long carbonic chains, and non-ionic surfactants such as polyoxyethylene sorbitan monolaureate (Tween 20, Tween 21, Span 20), monopalmitate (Tween 40, Span 40), monostearate (Tween 60, Tween 61, Span 60), tristearate (Tween 65, Span 65), monooleate (Tween 80, Tween 81, Span 80) and trioleate (Tween 85, Span 85). It should be noted that the use of a blowing agent/and/or a surfactant depends on the method of application (i.e., silk screening or mechanical film application), and the size and uniformity of the nanometal particles used in the formulation).

In a preferred embodiment, the present invention utilizes the gas sensitive material of $SnO_2$ nanocrystals doped with PdO and $In_2O_3$ in a gas detection or gas sensing device. (As used herein, the terms "gas detection" and "gas sensing", should be interpreted as being synonymous). As a part of a gas detection device, the gas sensitive material is deposited on a substrate, and is configured as a part of a circuit. By measuring the current, or changes in the current through that circuit gases may be detected, and the relative quantities of those gasses measured.

In one embodiment of the gas detection device, the substrate of the gas detection device is in communication with a heat source. This embodiment can include, for example, a configuration where the heat source is a layer of material bonded to the substrate and is configured to be resistively heated as part of a heating circuit. In this manner, the gas sensitive material may be maintained at an optimal or constant temperature while the current flowing through the gas sensitive material is measured.

An important aspect of the invention is the use of the combination of the surfactant (in particular, stearic acid; and the blowing agent (in particular, ammonium carbonate) as well as other components for the preparation of the gas sensitive layer from paste containing blend of $SnO_2$ and $In_2O_3$ powders doped with PdO. The PdO is produced, starting with a solution of $PdCl_2$, as for example $PdCl_2$ mixed with 5% solution ethyl cellulose in terpineol.

The combination of surfactant and blowing agent was introduced into the nanometal paste in order to increase the sensitive layer porosity and reduce particle aggregation.

The next step in creating the sensitive layer is to deposit the thin layer paste onto a substrate and heat to 120° C. to decompose the ammonium carbonate to produce the desired porosity. The stearic acid, unlike the other organic components, is linked to ions on the surface of the metal oxides, and thus decreases the interaction between the nanoparticles (see for example S. Takenaka et. al. Microporous and Mesoporous Materials 59 (2003)123-131).

The film is then heated/calcined to 450-500° C. to decompose the other organic species. The three step process decreases the physical interaction between the individual particles, thereby facilitating the formation of pores. The process optimizes gas passage through the metal oxide layer. The combination of the surfactant (preferably stearic acid) and the blowing agent (preferably ammonium carbonate), enables the production of a sensitive layer of high efficiency and very fast response.

Example I

Challenges to Producing Screen Printable Sense Layer Pastes $PdCl_2$ crystals are virtually insoluble in water and organic solvents commonly used for paste vehicles. An attempt was made to make paste with undisclosed $PdCl_2$ crystals added directly to the vehicle, however it has been found that the metal chlorides rapidly attack the stainless steel screens used for printing. It was also nearly impossible to keep the $PdCl_2$ from reacting with other paste components and dropping out of suspension before printing could be accomplished.

The very high surface area of the nanoparticle oxide powders makes it difficult to formulate screen printing vehicles and pastes with sufficiently high solids content. As the solids content is increased, the viscosity also increases rapidly and problems with leveling, deep screen marks and trapped air bubbles make it impossible to produce a satisfactory screen printed thick film. Conversely, when the solids content is reduced the viscosity decreases to a satisfactory level; however the low solids content makes the thick film very susceptible to cracking.

Other salts of Pd that can be suitable include (Ethylenediamine)palladium(II) chloride $Pd(H_2NCH_2CH_2NH_2)Cl_2$, Ammonium tetrachloropalladate(II) $(NH_4)_2PdCl_4$, Bis(acetonitrile)dichloropalladium(II) $PdCl_2.(CH_3CN)_2$, Bis(benzonitrile)palladium(II) chloride $(C_6H_5CN)_2PdCl_2$, and (2-Methylallyl)palladium(II) chloride dimer $[(C_4H_7)PdCl]_2$. Any palladium salt that readily dissolves in dilute HCl (aqueous) and that can be converted cleanly to an oxide of palladium without leaving significant residues at temperatures below about 600 deg. C. can be suitable.

These problems were overcome by a technique for impregnating the nanoparticle oxides with an aqueous solution of completely dissolved $PdCl_2$ salts and then removing the chlorine component during post processing of the nanoparticle powders. The development of a new organic vehicle and processing steps including calcining and three-roll milling also effectively reduced the very high surface area of the nanopowder mixture making it possible to produce a stable paste with very satisfactory screen printing properties.

Procedure for Producing Screen Printable Pd Catalyzed Sensor Paste

Prepare Palladium Chloride Solution

The first step in the paste production process is to completely dissolve $PdCl_2$ crystals in an aqueous solution with dilute HCl acid. The amount of HCl acid used in this procedure should be minimized, and is approximately equal to the weight of $PdCl_2$ solute that is required. To prepare a 2 wt. % aqueous solution of $PdCl_2$ the following steps were used;

Step 1. High purity $PdCl_2$ crystals (Aldrich 323373, 5N's purity) are thoroughly crushed in an agate mortar and pestle (Aldrich Z112496-1 set) or dry milled to obtain −200 mesh powders.

Step 2. Fill Pyrex beaker or bottle with 46.0 grams deionized water. Add 1.0 grams $PdCl_2$ powders (−200 mesh). Place magnetic stir bar in solution and set Pyrex beaker or bottle on hotplate with stirrer.

Step 3. Slowly add 3.0 g concentrated HCl acid (Columbus Chemical Industries, Inc., 2575DH, 36.5-38.0% HCl) to the aqueous solution. Heat solution to approximately 50-60 deg. C. while stirring until PdCl$_2$ crystals are fully dissolved. Cover or cap on Pyrex container should be slightly loose to relieve any vapor pressure buildup. After cooling to room temperature, the PdCl$_2$ should stay in solution.

The PdCl$_2$ powder mesh size is not narrowly critical. Any convenient mesh size, –325 up to about 100 mesh is preferred. Smaller PdCl$_2$ crystals dissolve more rapidly because of the higher surface area.

Pretreat Nanopowders with PdCl$_2$ Solution

In this process the SnO$_2$ and In$_2$O$_3$ nanopowders are coated or impregnated with the PdCl$_2$ catalyst, and then calcined to remove any remaining chlorine components.

Step 1. The starting powders, including 33.0 grams SnO$_2$ nanopowders (Alfa Aesar 44897, NanoTekR, 22-43 nm, 99.5%) and 3.6 grams In$_2$O$_3$ nanopowders (Aldrich 632317, 15-25 nm, 3Ns) are combined with 51 grams of de-ionized water and thoroughly mixed in a large mortar and pestle to form slurry. Approximately 0.1 grams of DS005 dispersant (Polymer Innovations) may be added to the mixture to promote uniform mixing.

Step 2. Add 40.0 grams of 2 wt. % PdCl$_2$ aqueous solution (0.8 grams PdCl$_2$ dissolved solids) to nanopowder slurry and mix thoroughly.

Step 3. Place mortar and pestle on hotplate and bake out water while crushing powder cake to obtain coarse reddish-brown powders after drying. Preferably, a motorized mortar and pestle is used, or an equivalent mortar grinder, where ever reference is made to a mortar and pestle, herein.

Step 4. Place dry powders from Step 3 in Pyrex beaker and bake at 200 deg. C. in air for about 2 hours in an electric furnace. During this step the powders should turn nearly black in color.

Step 5. At this stage the dried powders can be crushed with a mortar and pestle to pass a –80 mesh sieve if necessary. The powders may be difficult to grind due to compacting and sticking (larger, hard agglomerates should be discarded).

Step 6. The crushed powders (–80 mesh) are placed in an alumina crucible or dish and calcined at 500 deg. C. in air for about 3 hours in an electric furnace. After cooling the powders should appear light reddish-brown in color.

Step 7. After calcining, the powders should be crushed with a mortar and pestle to pass a –100 mesh sieve, larger hard agglomerates should be discarded. The sieved powders are now ready for paste formulation with an organic vehicle and three-roll milling.

Paste Formulation

The starting powders for this procedure have been calcined to remove all chlorine components and processed according to previous steps such that all powders pass a 100 mesh sieve.

Step 1. A suitable organic paste vehicle is prepared by completely dissolving 7.63 grams of ethyl cellulose binder (Dow Chemical, Ethocel Standard 4) in 36.7 grams of diethylene glycol butyl ether acetate solvent (Dow Chemical, Butyl Carbitol Acetate). The ethyl cellulose powder should be slowly added to the solvent while rapidly stirring in order to avoid gellation or clumping. Mild heating over a hotplate with constant stirring will help facilitate this process.

Step 2. After the binder has been completely dissolved in the solvent, then 3.42 grams of 2-Furoic Acid leveling-agent (Aldrich F20505, 98%) and 5.3 grams of Igepal CO-630 surfactant (Aldrich 542334-100G-A) are slowly added to the vehicle and stirred until completely dissolved. Other heterocyclic building block furans such as 3-Furoic acid can be substituted. Many of the commercially available non-ionic surfactants can be substituted for the Igepal CO-630. Some examples would include Polyethylene glycol hexadecyl ether (Croda International PLC), Nonylphenol polyethylene glycol ether (Union Carbide Chemicals & Plastics Technology Corp), and Polyethylene glycol sorbitan monolaurate (Croda International PLC).

Step 3. Weigh out 24.0 grams of –100 mesh processed SnO$_2$/In$_2$O$_3$, Pd catalyzed nanopowders and mix with 16.0 grams of as prepared organic vehicle at 3500 rpm in DAC150 FV-K Speedmixer (FlackTek, Inc.) until a uniform smooth paste is obtained.

Step 4. At this stage the sensor paste typically has hard agglomerates that must be removed by milling with a Ross model 52M 2.5×5 3-roll mill (about 10 passes) with the feed roller set at about 0.001 inch gap and the apron roller set at about 0.0005 inch gap. The 3-roll milling process is used to completely wet the nanoparticle powders with paste vehicles and surfactants that are required for high performance screen printing.

Vehicles that are used for electronics grade screen printing typically use ethyl cellulose organic binders and terpineol (mixed isomers), butyl carbitol acetate, or Texanol solvent systems with lower vapor pressures and relatively low toxicity. Usually non-ionic class surfactants are used with higher viscosity paste systems.

Step 5. After 3-roll milling the sensor paste may still contain some soft agglomerates that should be removed to prevent any screen clogging. This is accomplished by forcing the paste through a 325 mesh screen with a plunger pump or doctor blade.

Step 6. The viscosity of the paste may be adjusted downward by thinning with Butyl Carbitol Acetate solvent (Dow Chemical) if necessary to obtained optimum screen printing properties. Solvents such as Texanol (Eastman Chemical Co) or terpineol (mixed isomers) can also be suitable for thinning.

Performance Difference Between the Pd Sensor at 250° C. and Non-Pd Sensor at 450° C.

The sensor response to an analyzed gas is caused by the Langmuir adsorption of gas on a sensor surface followed by reaction of adsorbed gas with oxygen surface centers leading to electron liberation. The response intensity $$S \rightarrow k_r C_a C_o \qquad (1),$$

where $k_r$ is the reaction rate constant, $C_a$ is the concentration of adsorbed gas, and $C_o$ is the concentration of oxygen surface centers. With lowering of temperature, $k_r$ decreases following the Arrhenius law, but $C_a$, on the contrary, increases according well known Langmuir isobar relation approaching a limiting value at low temperatures as shown in FIG. 12 and FIG. 13.

Figure 14:
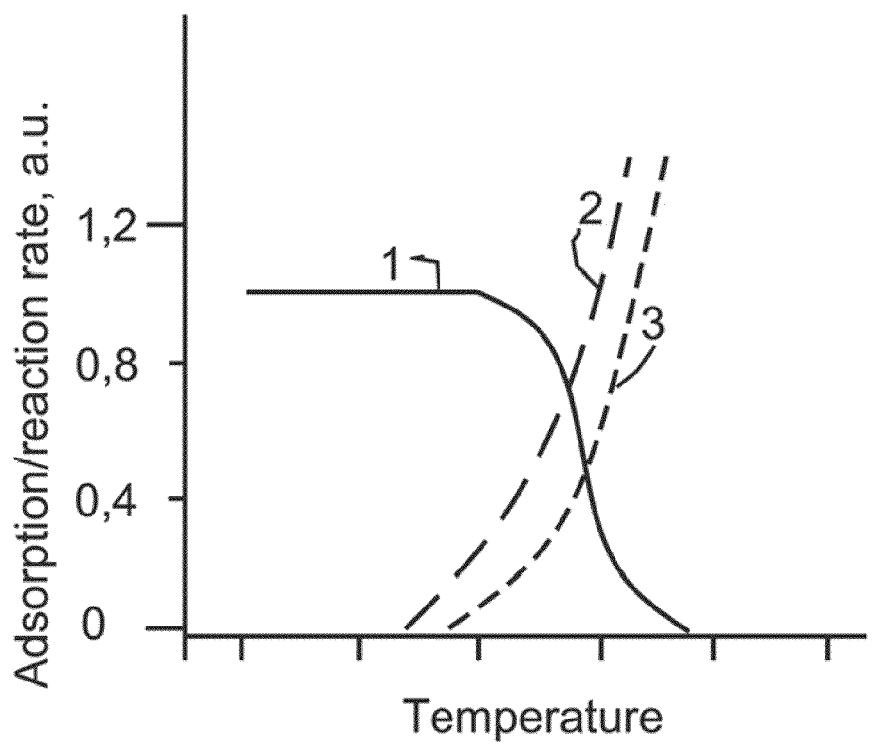
FIG. 14 is a plot showing the dependence of adsorption or reaction rate on the temperature, wherein; line 1—Langmuir isobar, 2—the rate constant of the reaction of analyzed gas with oxygen centers in the presence of Pd, and 3—the rate constant of the reaction of analyzed gas with oxygen centers without Pd.

FIG. 14 illustrates the dependence of adsorption or reaction rate on the temperature. In FIG. 14, 1 is the Langmuir isobar, 2 is the rate constant of the reaction of analyzed gas with oxygen centers in the presence of Pd, and 3 is the rate constant of the reaction of analyzed gas with oxygen centers without Pd.

The joint consideration of the Langmuir adsorption and the reaction terms in Eq. (1) gives the bell-shaped variation of the gas sensitivity with sensor operation temperature. Such temperature dependence of S with maximum ($S_{max}$) at the certain temperature ($T_{max}$) observed in our sensors is typical for semiconductor conductometric metal oxide sensors.

It should be noted that chemical reaction of metal oxide sensor with hydrogen is complex process including dissociation of H$_2$ to H-atoms on the sensor surface and subsequent reaction of H-atoms with oxygen surface centers leading to electron liberation:

$$H_2(ad.) \rightarrow 2H(ad) \qquad (1)$$

$$H(ad) + O-(ad) \rightarrow H_2O + e- \qquad (2)$$

It has now been found that the doping of metal oxide sensor with Pd greatly raises the sensor sensitivity to H$_2$ and decreases effective activation energy of overall sensing reaction. While the theory of the process is not part of the present invention, it is understood that the foregoing occurs because Pd-clusters, which are well known the most active catalyst of $H_2$-dissociation, promote this process in doped sensor. H-atoms, formed on Pd-clusters, transfer to metal oxide sensor and react with O— on metal oxide surface:

$$Pd + H_2 \rightarrow Pd + 2H(ad, Pd) \quad (3)$$

$$H(ad, Pd) \rightarrow H(ad, SnO_2) \quad (4)$$

$$2H(ad, SnO_2) + O—(SnO_2) \rightarrow H_2O + e-(SnO_2) \quad (5)$$

Figure 15:
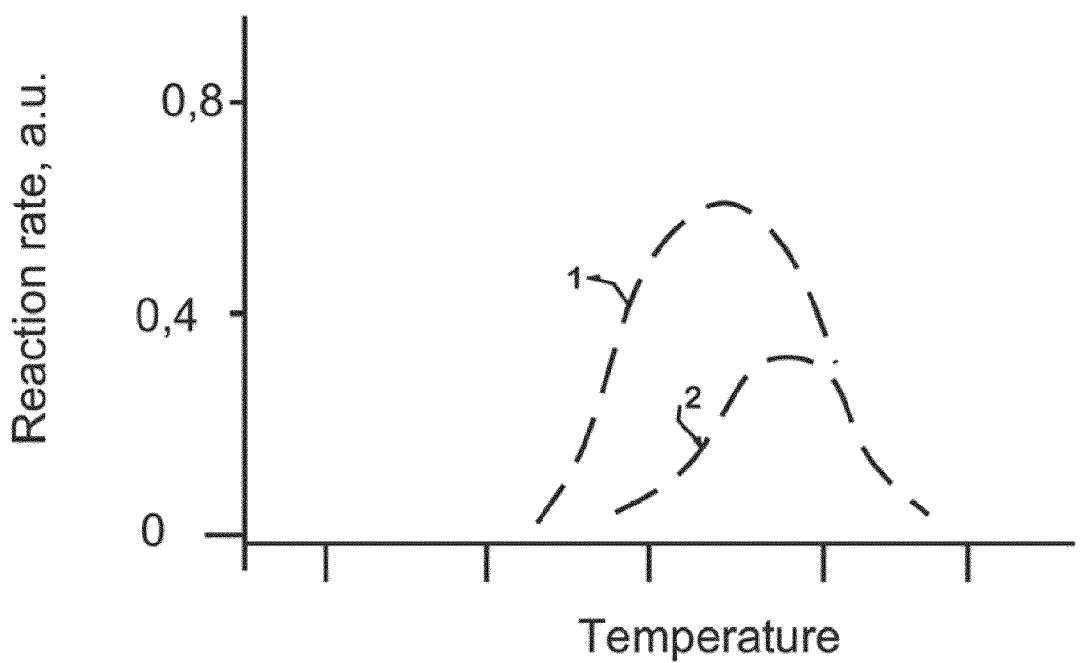
FIG. 15 is a plot showing the dependence of the reaction rate of analyzed gas with oxygen centers, in which line 1 represents with Pd and line 2 represents without Pd.

FIGS. 14 and 15 give the typical examples how the Langmuir adsorption and the sensing activated reaction terms vary with temperature and cooperate in reproducing the peculiar bell-shaped form of the gas response temperature dependence for metal oxide, in particular, $SnO_2$-sensor, on hydrogen without and with Pd. It can be seen that the increase of the sensor reactivity in the presence of Pd leads not only to the increase of $S_{max}$, but results in the shift of $T_{max}$ in the low temperature direction.

2. $H_2$ Detection and Conc. Range, and the Relative Response of the $H_2$ Sensor to CO and $CO_2$.

The sensors of the present invention can measure $H_2$—content in air in the range from 10 ppm to >6%. $H_2$ (v/v). They have no sensitivity to $CO_2$. The ratio $S_{co}/S_H$, where $S_H$ and $S_{CO}$ are sensitivities to $H_2$ and CO, respectively, depends on temperature, and is minimal at temperatures between 320 and 390° C.

3. Importance of Pd in Comparison to Non-Pd Sensors

The use of Pd dopant is important in metal oxide sensors on hydrogen and methane because Pd catalyzes the disruption of H—H— and C—H— bonds in these compounds and thereby activates sensor system. At the same time the doping of metal oxide sensors by Pd doesn't show marked effect on the sensor response to CO, so metal oxide sensors for CO detection can work effectively without Pd.

4. Theory of Sensors Without Pd

In the case of CO analyzed gas reacts directly with sensor surface $O^-$-centers and liberates e− without intermediate stages. $Pd^{+2}$-ions, as well as other two-valent ions, incorporated in $SnO_2$-lattice, create local electron levels in forbidden band of $SnO_2$— semiconductor and thereby influence the sensoring reaction, but this effect of Pd is rather weak.

The $H_2$-detecting by metal oxide sensor includes the intermediate stage of $H_2$-dissociation to H-atoms on the sensor surface. Without Pd this dissociation reaction proceeds with participation of radical-type surface defects, such as, for example, surface uncharged oxygen vacancies in $SnO_2$.

In this case, dissociation requires high activation energy because such defect centers have rather low reactivity. Pd doping of $SnO_2$ leads to formation of highly reactive Pd-catalytic centers, which promote $H_2$-dissociation, decreasing activation energy of this process in comparing to situation without Pd and so greatly increase sensor sensitivity.

Sensor Physical Differences

General Description of Systems

The sensor formulation and, production method, and operating conditions of the present invention are based on a complicated set of chemical and physical processes that alter overall sensor sensitivity, dynamic range, specificity to different reducing gases, and response and relaxation times. Table 1 summarizes these various factors and performance characteristics, and is described in detail in the examples.

TABLE 1

Physical and Chemical Characteristics, and Performance of Sensitive Layers Having 10 to >100 nm Nanospheres Following Mixing of Oxides, or Milling for particle Uniformity

| Film Layer Type | Sense Layer Thickness (μm) | Gross Porosity[a] | Contact Porosity[b] | Particle Size (nm) | Specific Surface Area[c] (m$^2$/gm) |
|---|---|---|---|---|---|
| 1) A016 | ~800 | High | Med | ~100-900+ | ~7 |
| 2) 2HC | ~350 | Med | High | ~30-400 | ~10 |
| 3) P9 | ~400 | Med | High | ~20-50 | ~10 |
| 4) P15 | ~400 | Med | High | ~20-50 | ~10 |
| 5) SI-1 | ~100 | Low | High | ~20-40 | >20 |
| 6) 2PG | ~11 | Low | High | ~10-20 | >50 |

| Film Layer Type | Pd Form[d] | Active Center Saturation[e] (95% at % H) | Response/ Relaxation Time (sec)[f] | Specificity and Discrimination[g] | | | |
|---|---|---|---|---|---|---|---|
| | | | | H | CO | CH$_4$ | CO$_2$ |
| A016 | no Pd | 1.5-2 | <3-4/20-30 | M | M | M | E |
| 2HC | PdO | 1.5-2 | 1-3/10-20 | M | M | M | E |
| P9 | no Pd | 1.5-2 | 2-5/10-30 | M | M | M | E |
| P15 | PdO | 1.5-2 | 1-3/10-20 | M | M | M | E |
| SI-1 | PdCl$_2$/oxide | ~4 | 1-2/5-20 | E | E | E | E |
| 2PG | PdCl$_2$/oxide | >6 | 1-2/5-15 | E | E | E | E |

[a]Gross porosity included the deep and fractures/channels (100-1000 nm) formed during the layer processing.
[b]Contact porosity is an estimate of the ~100 Angstrom spacing left between the contact points between nanoparticles, after removal of the surfactant during calcining.
[c]Calculated/estimated based on nanometal particle sizes and film thickness.
[d]No Pd; Pd supplied at PdO$_2$; Pd supplied as PdCl$_2$, and likely converted to a thin film oxide coating on the Sn and In nanoparticles during calcining
[e]The conc of H$_2$ that appears to be saturated at indicated H$_2$ conc.
[f]Dynamic exposure system with rapid clearing/equilibration of sensor atmosphere; diffusion only required between flash suppressor and sensitive layer. Response/relaxation times, at 90% of final value.
[g]Gas response: sensitivity to H$_2$, and discrimination against CO$_2$, CO and CH$_4$ are rated as moderate (M), or excellent (E) discrimination.

Sensor design with the common Sn/In type sensors are the "A" group of Table 1. These sensors have been modified to improve both particle size of the nanometals and their physical association which affect the required quantum requirements of the active centers; namely number of active centers, the ~100 A spacing requirement for the association of the reducing gases to engage in the electron transfer process, gas specificity, and to provide for rapid response and relaxation times.

Improved performance has been achieved through the manipulation of particle size, layer porosity and manipulation of the Pd activator using spray application techniques, and silk film production. Organic surfactants and a blowing agent have been used to control what is perceived as the gross porosity of the sensing layer, and the molecular level separation of the active centers and control of the proximity of the activator (Pd), respectively.

The groups of sensors compared in Table 1 include sensitive layers composed of: Sn/In alone (A016 and P9), Sn/In and Pd oxide nanoparticles (3HC and P15), and Sn/In with PdO added as a soluble $PdCl_2$ (SI-1 and 2PG), then converted thermally to the oxide. All samples were produced with some form of surfactant and/or a blowing agent. A blowing agent is particularly critical with thicker sensitive layers to improve porosity, and less important when the sensitive layer is thinner as with SI-1 (spray application) and 2PG sensors which employs silk screening for application of the smaller nanoparticles. Based on the test data for these various sensor types that resulted in the final 2PG type, it would appear that sensor performance is a function of a number of factors:

the number of active centers, controlled by nanometal particle size and molecular spacing within the sensitive layer the elimination of large particles which reduce the spatial contact at the active center, and the use of soluble $PdCl_2$, to coat the other nanoparticles (Sn and In), prior to thermal conversion of the chloride to the oxide state.

It appears that this dispersion of the Pd activator, compared to the oxide form, results in a pronounced effect on dynamic sensing range (0.005 to >6% $H_2$) by increasing the number of functional active centers, and improving specificity compared to other reducing gases, and improving response time.

Hydrogen Performance

Using prior art variations in Sn oxide compositions, hydrogen can be detected, but commercially available sensors suffer from deficiencies. These deficiencies include, limited dynamic concentration range 0.01 to ~1.5% $H_2$, poor selectivity with respect to reducing gases such as $CO_2$, CO and $CH_4$, and have slow response and/or relaxation times.

It has now been found that there is a need to improve the sensor/sensitive layer to address the theoretical chemical and physical parameters that would optimize both the porosity (access to active centers), number of reaction centers, and spatial/thermodynamic requirements of the active center.

In accordance with an embodiment of the present invention, an improvement can been obtained by employing surfactants to provide the required ~100 A spacing (molecular porosity) between the contacting nanoparticles, by using blowing agents to increase gross porosity (particularly for thicker films, (>200 μm), and through the use of Pd oxide, using Pd chloride as an activator in the sensing process, to coat the Sn/In nano-particles.

In accordance with a preferred embodiment of the invention, the Pd contact with the Sn- and In-oxide particles can be optimized through the use of soluble $PdCl_2$, rather than PdO particles. It is believed that the use of $PdCl_2$ results in a molecular coating of non-refractory oxides onto the Sn and In particles, and this improves the action of the Pd as the activator in the gas interaction process.

Figure 3:
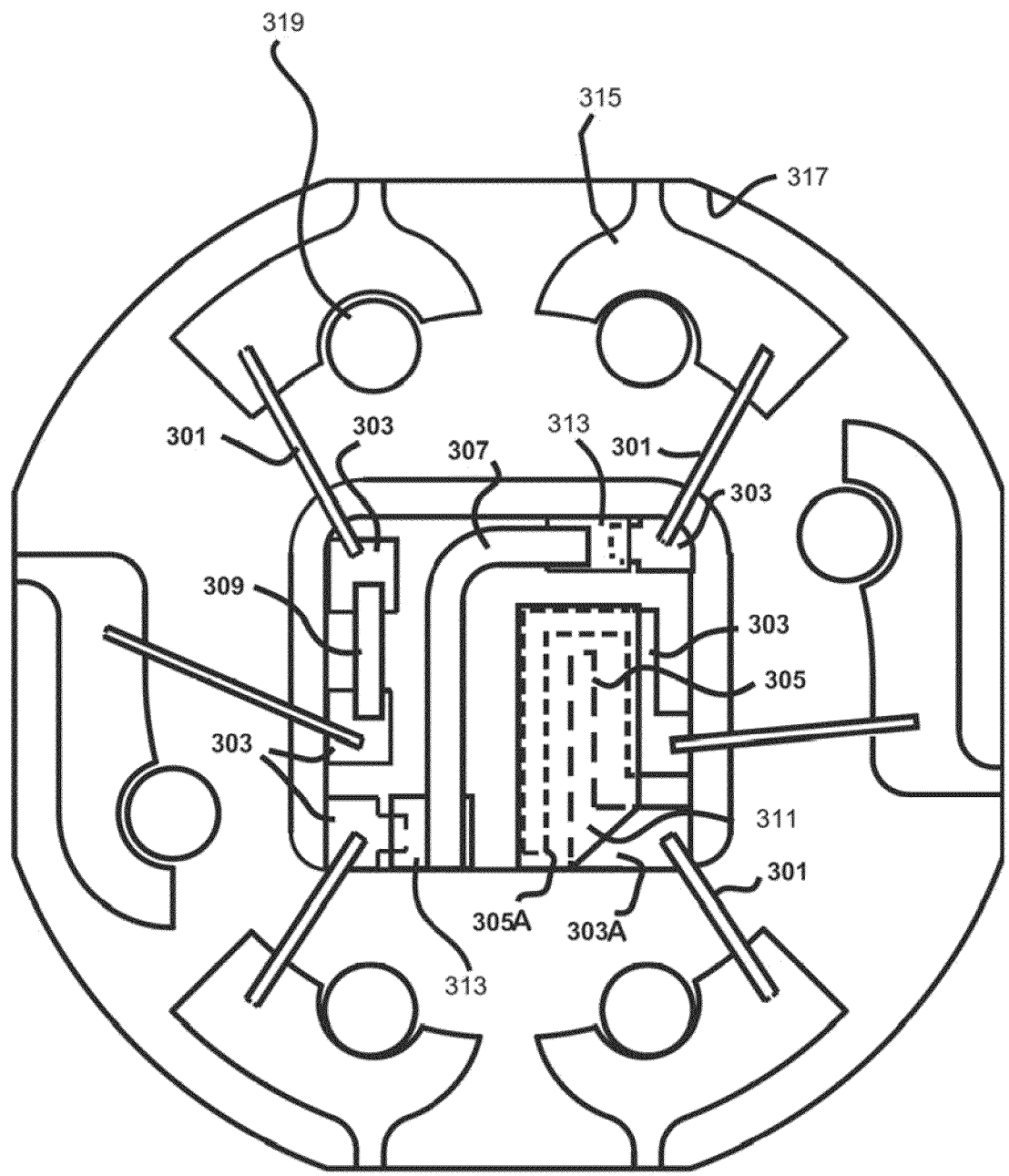
FIG. 3 shows a sensitive layer silk screened onto the upper surface of a test platform, containing a heater, and al termistor for temperature control.

The sensor of FIG. 3 is suspended from frame 317 by wire bonds 301. Gold pads 303 form a bond with the wire bonds 301. The other end of each wire bond 301 is in contact with gold wire bond pads 315 located on the frame section 317, of the ceramic substrate. The wire bonds 301 connect to the pads on the chip section of the substrate and to the pads on the frame section, the outer edge of which is shown as 317. A sensor layer 311 contacts one wire bond via gold pad 303 and another wire bond via gold pad 323. Section 333 of gold pad 323 lies under the sense layer 311. Similarly, gold pad section 313 of gold pad 303 lies under the sense layer 311.

Silver pads 313 are used to terminate the heater 307. The silver pads are in contact with gold pads, which in turn, contact the gold pads 315 via wire bonds 301.

The outside edge of each holes 319 is machined in the substrate, The pins from the T-05 header will slip through the holes 319, The gold pads 315 that surround the holes 319 and the pin from the header are connected with conductive epoxy.

Thermistor 309 is terminated at each end by gold a gold pad 303, which in turn make contact with the gold pads 315, via wire bonds 301.

Figure 4:
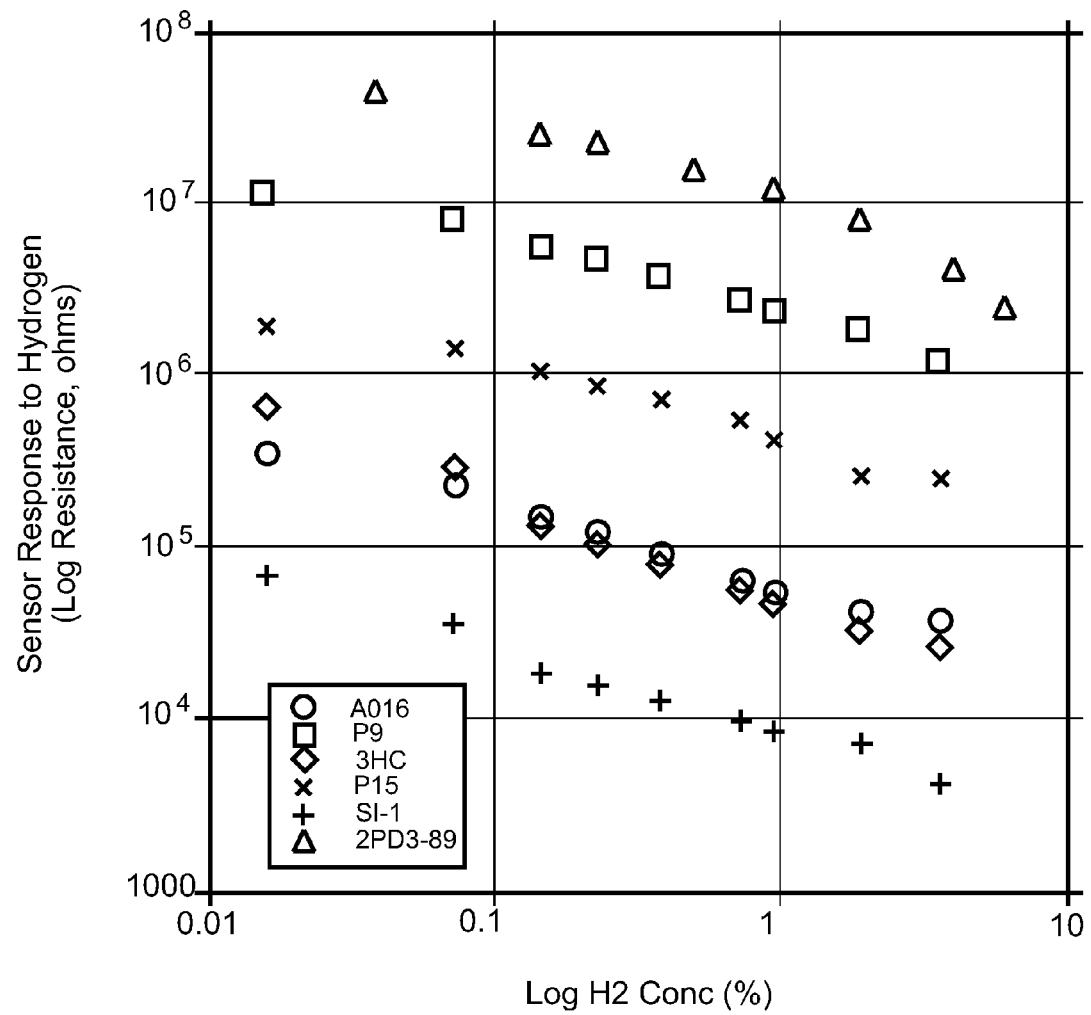
FIGS. 4 and 5 are typical linear and log plots of sensor resistance versus $H_2$ concentration, based on formulation and physical properties of the sensitive layer.
Figure 5:
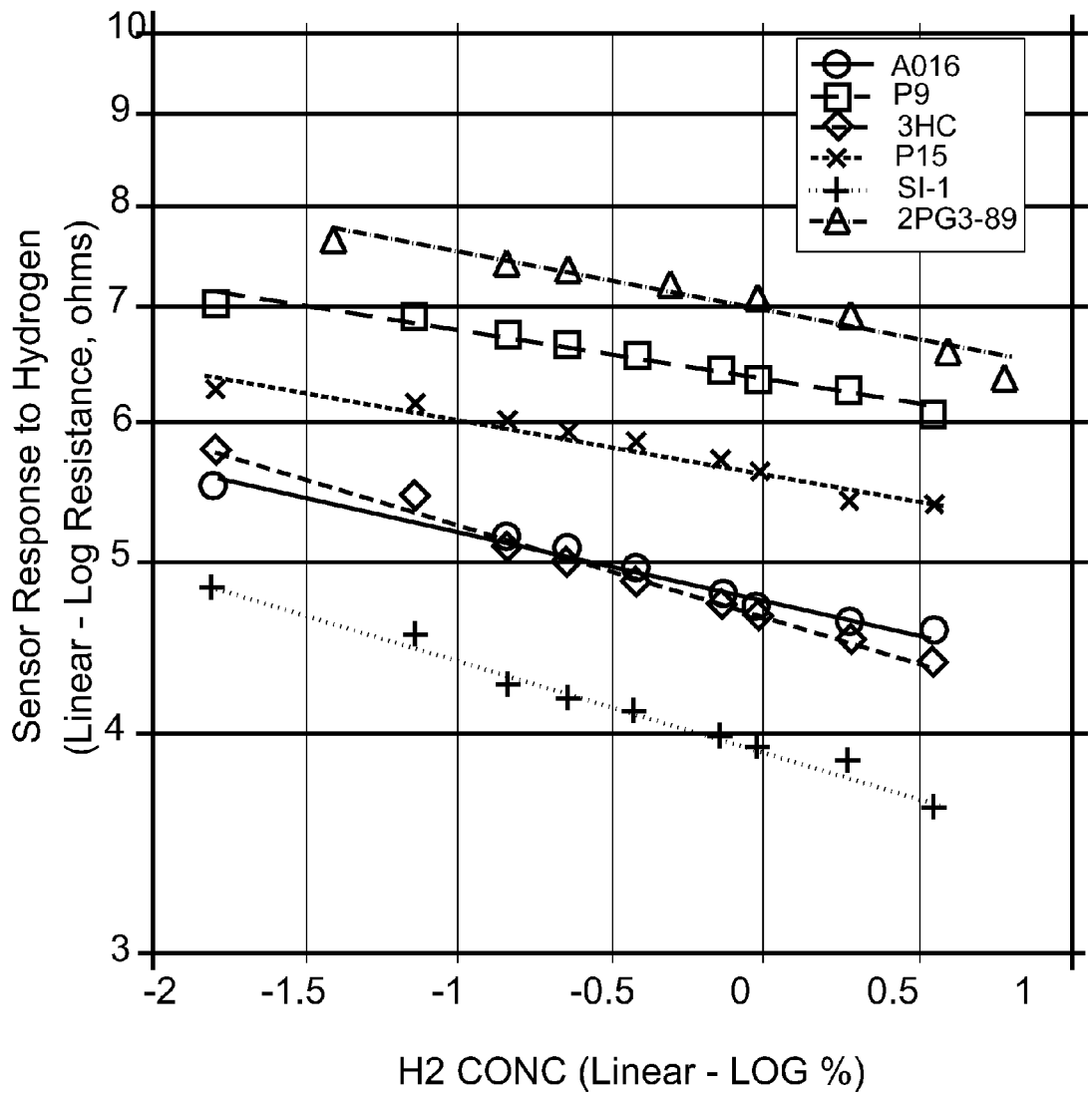
Figure 6:
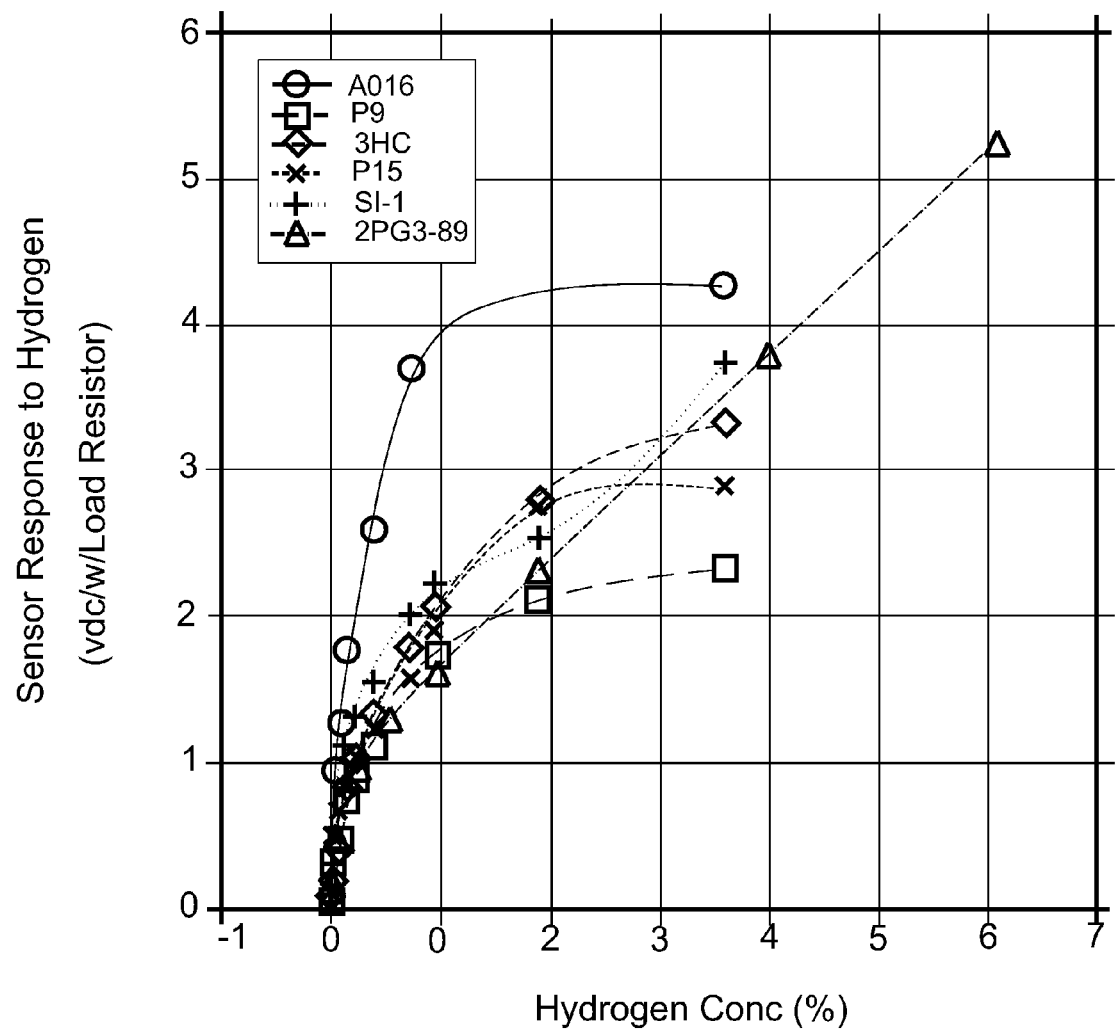
FIG. 6 is a linear plot of hydrogen response, using a series load resistor to obtain sensor response in VDC.

FIGS. 4 and 5 provide typical log-log and lin-log plots of sensor resistance versus $H_2$ concentration. These log plots show no dramatic/obvious differences in slope for sensors, with no Pd, with PdO, or with $PdCl_2$ However, there is an indication in the plots of a slight slope change between 1-2% $H_2$ for the no Pd (A016, P9) and PdO (3HC, P15), and the $PdCl_2$ (SI-1 and 2PG) sensors. In the no Pd and PdO sensor formulations the slopes between 1 and 4 or 6% tend to decrease, while the $PdCl_2$ sensors increase at >2% $H_2$. This trend is best observed in linear plots of hydrogen response, using a series load resistor to obtain sensor response in VDC, as seen in FIG. 6. In comparing the concentration response of the no Pd (A016 and P9), PdO (3HC and P15), and $PdCl_2$ (SI-1 and 2PG) sensors, it is clear that the no Pd and PdO sensors, become less concentration sensitive at $H_2$ concentrations between 1 and 2% $H_2$, while the $PdCl_2$ sensors SI-1 and 2PG show no apparent saturation in sensor sensitivity, and show good concentration at >4 and >6% $H_2$, respectively.

While the theory of the mechanicals of the processes is not part of the present invention, by way of background only, it is submitted that the data indicates that the use of $PdCl_2$, dramatically increases the number of active centers. Additionally, it is surmised that the number and access to active centers have been optimized by the smaller nanometal Sn- and In-oxides produced in the milling process, and it appears that the soluble $PdCl_2$ is more effective in coating the Sn and In particles while the chloride is in soluble form and dispersed when finally calcined at high temperature.

Role of Temperature in Sensor Response to Hydrogen

Figure 7:
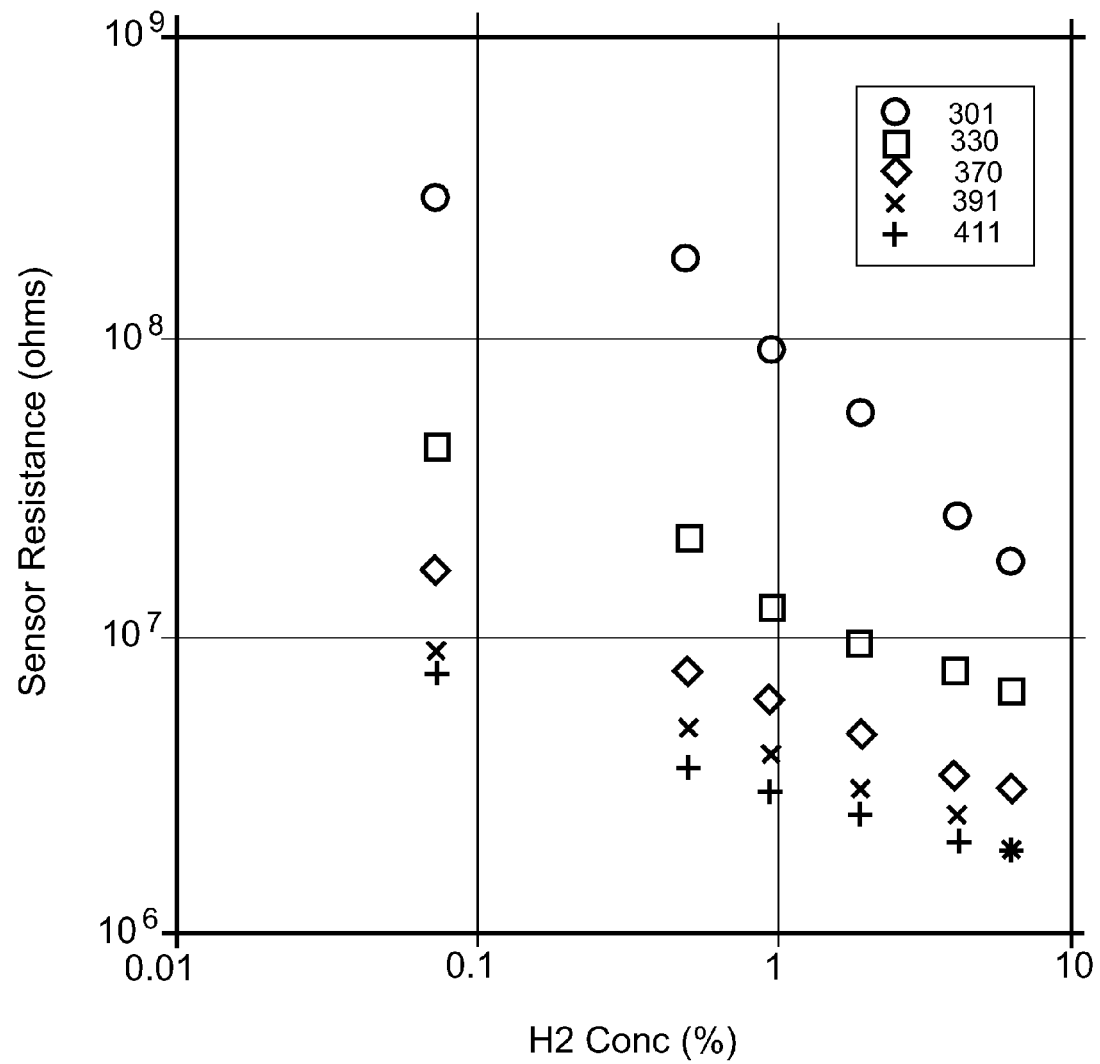
FIG. 7 is a log response plots for a single $PdCl_2$ sensor operated between 301 to 411° C. (temperature optimum for $H_2$ is between 330 and 390° C.)
Figure 8:
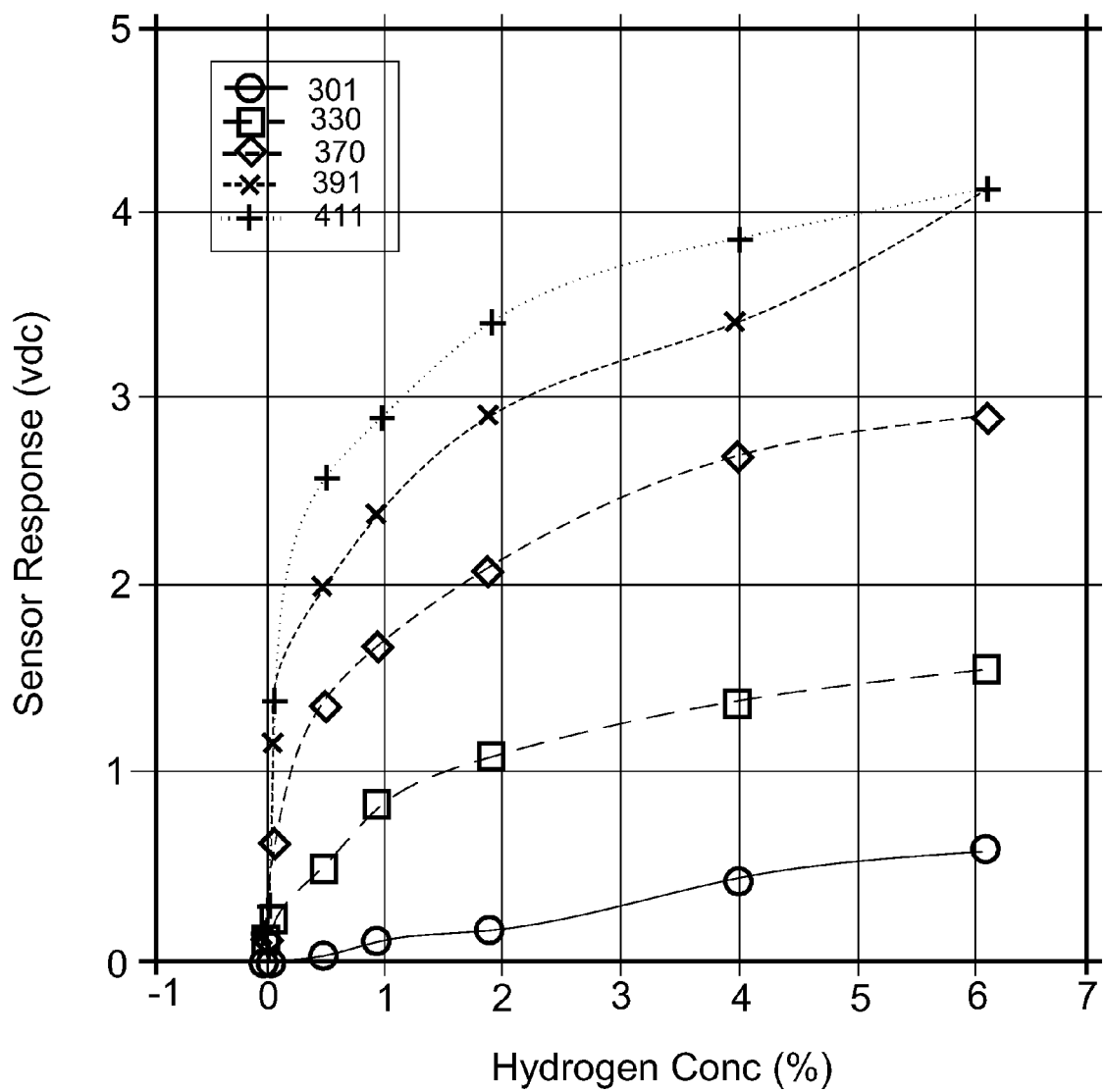
FIG. 8 is a linear plot of sensor response in VDC using a series load resistor.

Thermodynamically, the Sn/In/Pd sensors have predictable thermal requirements for effective function of the active centers. During sensor heater and platform redesign, careful attention was paid to the actual rather than the calculated temperature of the sensitive layer, and the influence of temperature on $H_2$ response. FIGS. 7 and 8 provide the typical log-resistance and linear response based on sensor film resistance. The log response plots (FIG. 7) for a single $PdCl_2$ sensor operated between 301 to 411° C. show the expected reduction in overall resistance with increasing temperature, and a noticeable reduction in the slope at temperatures below 350-370° C. At 301° C. the slope is steeper, but as will be described later, selectivity to other reducing gases is poorer at lower temperatures (<390° C.). The linear plots (FIG. 8) of sensor response in VDC using a series load resistor clearly show an optimum $H_2$ response at 350-411° C. VDC. At this temperature, response is good, and linearity at concentrations above 6% $H_2$ can be attained.

Influence of Other Reducing gases and Carbon Dioxide on Hydrogen Response Signal Carbon Monoxide.

Carbon monoxide is a reducing gas that can significantly (10-30% of $H_2$ signal) affect the $H_2$ signal from a $H_2$ sensor, or give a false positive signal in the absence of $H_2$. Table 2 provides a comparison of a series of formulated sensitive layers, operated at 400 and 330° C. In this study, each sensor was exposed to $H_2$ at 0.039% in air, and the signal compared to a series of CO concentrations in the absence of $H_2$. The objective was to determine the response of no Pd, with PdO and with $PdCl_2$, on sensor response and sensor selectivity to $H_2$. The point of comparison was the concentration of CO needed to yield a false positive $H_2$ signal equivalent to 0.039% $H_2$.

At 330° C., the no-Pd sensor exhibits a significant (compared to 0.039% $H_2$) at 0.155% CO. The $PdO_2$ sensor shows a $H_2$ equivalent response (0.039% $H_2$) only at a CO concentration slightly less than 1.43% CO. The Pd $Cl_2$ sensors again show an equivalent H2 response much greater than 2.17% CO.

At 330° C., a comparison of the $H_2$ signal at 0.039% and the CO signal with increasing CO concentration, shows the order of sensitivity to CO to be no $Pd > PdO_2 > PdCl_2$, with the 0.039% $H_2$ equivalent signal being at approximately 0.15, 1.4 and >>2% CO in air At 400° C., the no Pd sensors (17a and 12a) show a signal at 0.155% CO (underscored CO values) equivalent to 0.039% $H_2$. The PdO sensor shows a $H_2$ equivalent response only at a CO concentration >2.17% CO. The Pd $Cl_2$ sensors show an equivalent much >2.17% CO.

Figure 9:
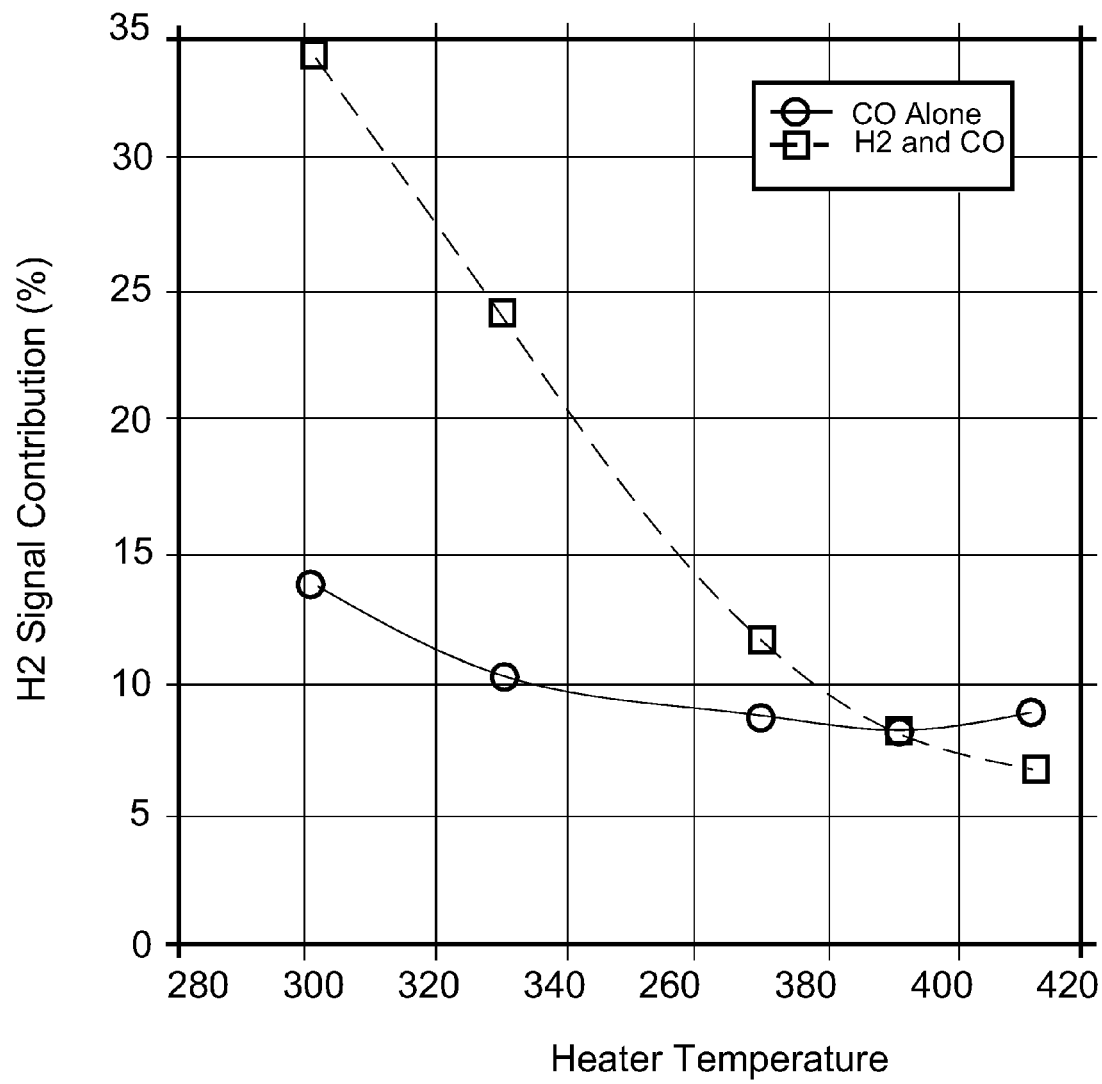
FIG. 9 shows a plot of the relative signal contribution of CO alone and CO+$H_2$.

FIG. 9 shows the relative sensitivity of the $PdCl_2$ 2PG sensor with operating temperature. The plot shows sensor response to CO (0.8%) alone and CO (0.68%) with $H_2$ (0.5%), at sensor temperatures from 310 to 410° C. The $H_2$ signal contribution is the effect that CO has on the $H_2$ only signal at 0.5%. The resulting calculation shows that while CO and $H_2$ together are sensed at a higher response level than $H_2$ alone as expected. However, while $H_2$ response signals are additive at 300 to 370° C., with the typical 30% increase in response, they decline to ~8% at the optimum sensor temperature of 370 to 400° C.; this in the case where CO concentration actually exceeds the $H_2$ concentration in air.

TABLE 2

Influence of sensor formulation on specificity of hydrogen sensors to CO.

| Temp (° C.) | Formulation | Hydrogen Signal (vdc) (at 0.039% $H_2$) | CO Conc (%) | CO Signal (vdc) |
|---|---|---|---|---|
| 400 | P12a no Pd | 1.077 | 0 | 0.149 |
| | | | 0.068 | 0.516 |
| | | | 0.155 | 0.693 |
| | | | 0.682 | 1.41 |
| | | | 1.43 | 2.3 |
| | | | 2.17 | 2.58 |
| | P22a $PdO_2$ | 2.531 | 0 | 0.096 |
| | | | 0.068 | 0.207 |
| | | | 0.155 | 0.292 |
| | | | 0.682 | 0.609 |
| | | | 1.43 | 0.84 |
| | | | 2.17 | 0.922 |
| | | 2.81 | 0 | 0.144 |
| | P8a $PdCl_2$ | | 0.068 | 0.158 |
| | | | 0.155 | 0.185 |
| | | | 0.682 | 0.23 |
| | | | 1.43 | 0.276 |
| | | | 2.17 | 0.317 |

TABLE 2-continued

Influence of sensor formulation on specificity of hydrogen sensors to CO.

| Temp (° C.) | Formulation | Hydrogen Signal (vdc) (at 0.039% $H_2$) | CO Conc (%) | CO Signal (vdc) |
|---|---|---|---|---|
| 330 | P17a no Pd | 0.65 | 0 | 0.127 |
| | | | 0.068 | 0.325 |
| | | | 0.155 | 0.458 |
| | | | 0.682 | 0.955 |
| | | | 1.43 | 1.405 |
| | | | 2.17 | 1.55 |
| | P22a $PdO2$ | 3.175 | 0 | 0.415 |
| | | | 0.068 | 0.99 |
| | | | 0.155 | 1.54 |
| | | | 0.682 | 2.83 |
| | | | 1.43 | 3.402 |
| | | | 2.17 | 3.633 |
| | P11b PdCl2 | 3.36 | 0 | 0.043 |
| | | | 0.068 | 0.062 |
| | | | 0.155 | 0.075 |
| | | | 0.682 | 0.109 |
| | | | 1.43 | 0.159 |
| | | | 2.17 | 0.214 |

Figure 10:
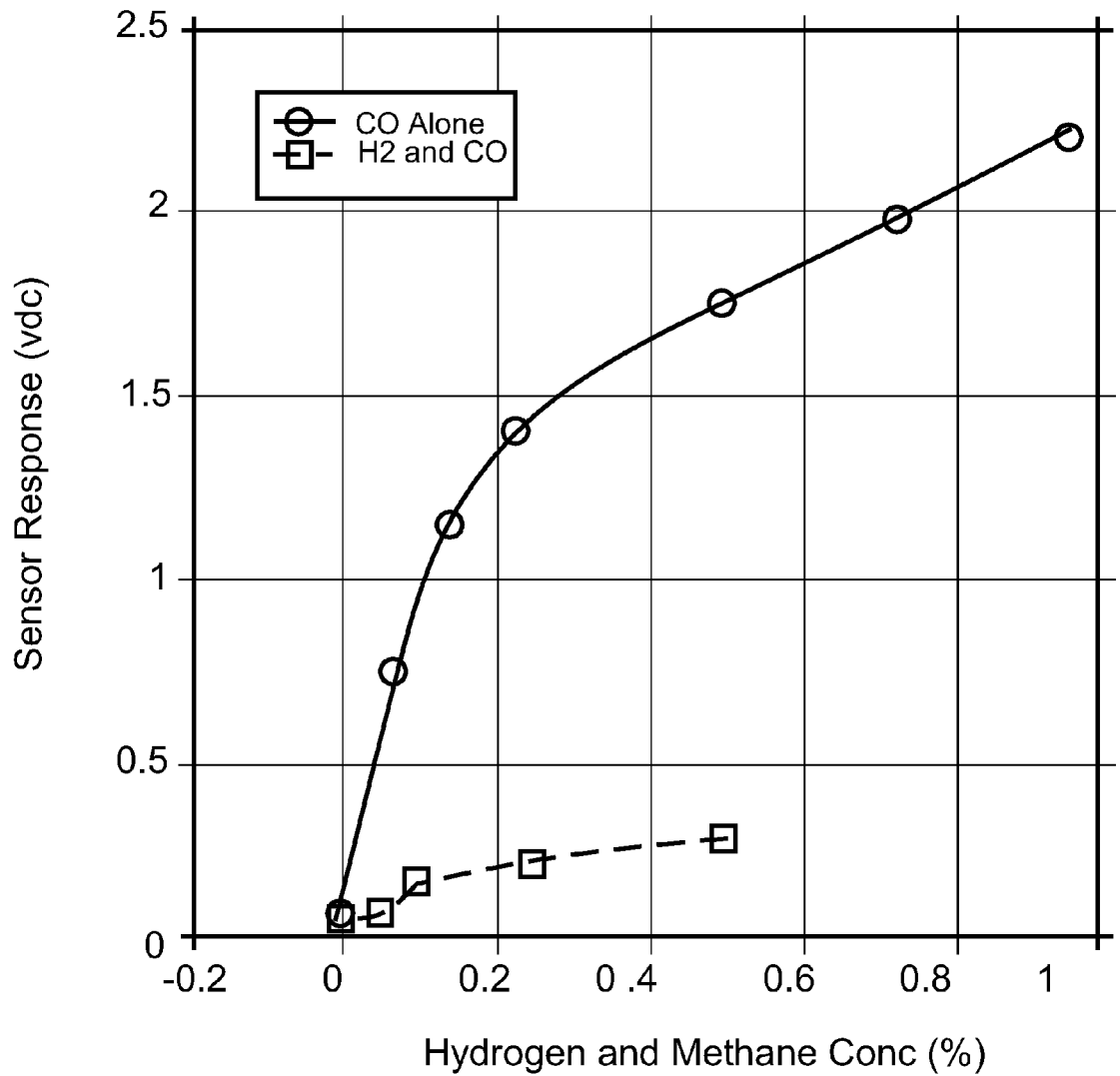
FIG. 10 is a plot of a $PdCl_2$ formulated sensor showing relative response to hydrogen and methane.
Figure 11:
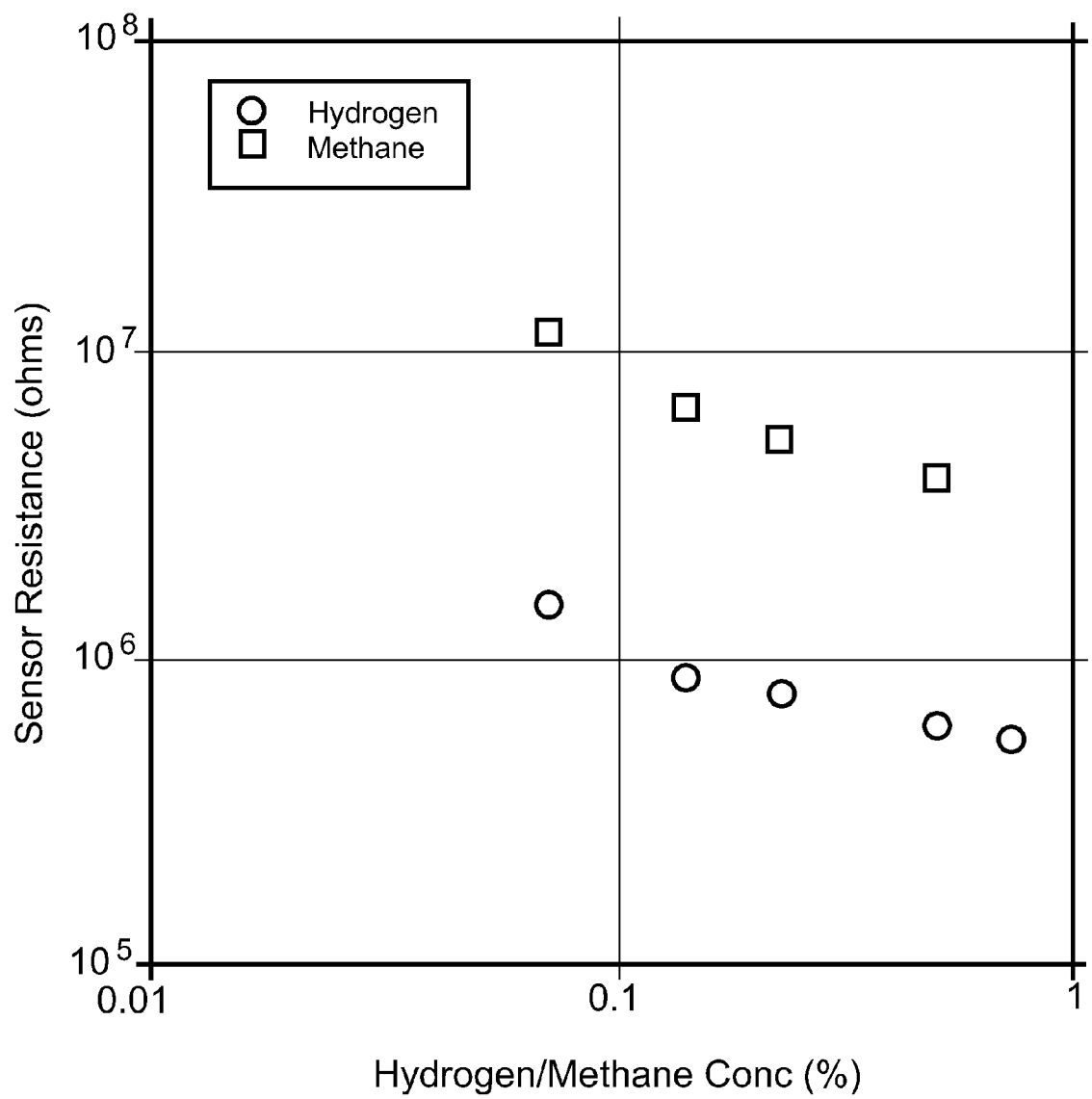
FIG. 11 is a log plot of $PdCl_2$ formulated sensor, relative response to hydrogen and methane.

Methane. Methane is a reducing gas that would normally contribute a significant signal for the normal Sn/In-based $H_2$ sensors. With the $PdCl_2$ formulated sensors, selectivity for hydrogen is much higher for Hydrogen than for methane. FIGS. 10 and 11 provide the linear signal plots and log-resistance base on gas concentration. In both plots, the methane offset both in sensor resistance and the voltage response across an in series load resistor, show a significant discrimination against methane. The actual contribution of methane compared to hydrogen on sensor response is tabulated in Table 4. When the sensor operated at 405° C. is exposed to 0.05% $CH_4$ in air, the resulting sensor signal is 6% of the 0.5% $H_2$ signal, and at 0.5% $CH_4$ the signal is 18% of the $H_2$ signal. Slight reduction in operating temperature to 343° C., has only a marginal effect on signal response, 9 and 17%, respectively. When the $PdCl_2$ sensor is exposed to both $CH_4$ and $H_2$ at 0.5%, the resulting signal is 94-97% of the 0.5% $H_2$ alone signal. It is unclear why the signal is not additive, since the normal affinity of these types of sensors for methane is high.

TABLE 4

Influence of sensor temperature on specificity of methane compared to hydrogen; $H_2$ at 0.5%, $CH_4$ at 0.05 and 0.5% (2PG)

| Sensor | Gas Test Mixture | Change in Sensor Signal (% in Air)[a] | |
|---|---|---|---|
| Temp (° C.) | $CH_4/H_2$ | $CH_4$ Alone | Hydrogen + $CH_4$ |
| 405 | 0.05/0 | 6.3 | |
| | 0.5/ | 18.4 | |
| | 0.5/0.5 | | 94.4 |
| 343 | 0.05/0 | 9.0 | |
| | 0.5/0 | 17.4 | |
| | 0.5/0.5 | | 97.7 |
| 405 | 0.05/0 | 6.3 | |
| | 0.5/0 | 18.4 | |
| | 0.5/0.5 | | 94.4 |
| 343 | 0.05/0 | 9.0 | |
| | 0.5/0 | 17.4 | |
| | 0.5/0.5 | | 97.7 |

[a]Percent $H_2$ in air signal at 0.5%

Carbon Dioxide.

The $PdCl_2$ formulated sensors have shown no detectable effect offset of $CO_2$ on either $H_2$ detection, or a signal up to 2% $CO_2$. In fact, $CO_2$ has a minor influence in that it reduces $H_2$ response by about 2% at $CO_2$ concentrations >1.2%.

Response to VOC's. Volatile organic compounds present problems with respect to both false positive signals and reliability of all current sensor types. The former is a problem of signal response from other than the target gas, and irreversible poisoning or damage to the sensitive layer and its response to $H_2$. The current $PdCl_2$ sensor was evaluated based on the UL 2075 VOC contaminant list as shown in Table 3. Results indicated that there was little or no response to methane, carbon dioxide, carbon monoxide or butane at the specified 500 to 5000 ppm exposure. Notable is the fact that while there was a signal response to all of the complex organic compounds, the sensitive layer was not damaged and responded to $H_2$ normally after the exposure to all of these VOC's.

TABLE 3

Table 2 Response and recovery for UL 2075 Contaminants in Air

| Test Parameter | Value | H2 Equiv Resp | Recovery Time | Permanent Effect |
|---|---|---|---|---|
| Methane | 0.5 vol % | <0.026% | rapid | none |
| Carbon Dioxide | 1.83 vol % | <0.026% | rapid | none |
| Carbon Monoxide | 1.4 vol % | <0.026% | rapid | none |
| n-Butane | 300 ppm | <0.026% | rapid | none |
| n-Heptane | 500 ppm | 0.1% | rapid | none |
| Ethyl Acetate | 200 ppm | 0.7% | 10 min. | none |
| Isopropyl Alcohol 200 ppm | 1.2% | rapid | none | |
| Ammonia | 100 ppm | 0.1% | rapid | none |
| Ethanol | 200 ppm | 0.6% | rapid | none |
| Toluene | 200 ppm | 0.5% | rapid | none |
| Acetone | 200 ppm | 0.7% | 30 min | none |

It is clear from the results from the two preparation methods employing either unprocessed nanoparticles or milled nanoparticles, that particle size is one of several critical aspects of these nanometal sensors. The other factors which appear to be interrelated, are the use of the surfactant to provide molecular/contact spaces between the nanoparticles, the use of dispersed Pd by the use of $PdCl_2$, the use of a blowing agent to form gross porosity with thicker films, and use of critical operating temperatures.

The transition from irregular shaped to spherically sized nanoparticles (few/distributed large pores (i.e. >1 micron), results in the smallest particles appearing to be on the order of 100-500 nm in diameter, resulting from more uniform milled nano-spheres (10-40 nm spheres, 100-150 nm clusters, with few major pores 50-150 nm), provided the basis for increasing the specific surface of the sensitive layer, and increasing the number of available active centers. The use of an organic surfactant to provide the molecular spacing between particles, likely increased the dynamic range of the sensor. The factor which actually allowed all of the above system components to come together was the use of $PdCl_2$. The performance of the soluble $PdCl_2$, compared to no Pd, or PdO, likely results from the dispersal of the soluble activator within the surfactant, and a rather uniform coating of the other oxide particles. On thermal processing at 500° C. the blowing agent is decomposed, while the $PdCl_2$ is converted to Pd-oxides as a distributed rather than large particles as with the Pd-oxides.

All of these factors combined to provide a sensitive layer that can be operated at higher temperatures, thus affecting overall performance. The key attributes of the current sensor are:
   1) low end sensitivity, and linear response over 0.015 to 1% for $H_2$,
   2) wide dynamic sensing range of 0.015 to >6%,
   3) good response and relaxation times (at 0.2% $H_2$, 1 and 3 sec respectively)
   4) excellent selectivity for $H_2$ compared to CO,
   5) good selectivity for $H_2$ compared to $CH_4$, and
   6) no sensitivity to $CO_2$.

Formula for Sensor Paste Experiment #5 Used in the Manufacture of P15 Parts
Palladium infused Indium Tin Oxide (ITO) Powder Formula from Sensor Paste Experiment #5

| grams | material | wt % |
|---|---|---|
| 5 | $SnO_2$ | 88.21% |
| 0.55 | $In_2O_3$ | 9.70% |
| 0.118 | $PdCl_2$ | 2.08% |
| 5.668 | | 100.00% |

Solvent Preparation

| gram | material | wt % |
|---|---|---|
| 0.292 | ethyl hexanol | 27.06% |
| 0.593 | Butyl carbitol | 54.96% |
| 0.194 | Ethocell 10 | 18.0% |
| 1.08 | | 100.00% |

Paste Formulation

| grams | material | wt % |
|---|---|---|
| 4.27 | ITO powder Exp #5 | 76.25% |
| 1.08 | Solvent preparation | 19.29% |
| 0.25 | Oleic acid | 4.46% |
| 5.6 | | 100% |

Formula for Sensor Paste Experiment #7 Used in the Manufacture of P9 Parts
NO Palladium Infusion
Indium Tin Oxide (ITO) Powder Formula from Sensor Paste Exp #7

| grams | material | wt % |
|---|---|---|
| 5 | $SnO_2$ | 90.09% |
| 0.55 | $In_2O_3$ | 9.91% |
| 0 | $PdCl_2$ | 0.00% |
| 5.55 | | 100.00% |

Solvent Preparation

| gram | material | wt % |
|---|---|---|
| 0.2706 | ethyl hexanol | 27.06% |
| 0.5496 | Butyl carbitol | 54.96% |
| 0.18 | Ethocell 10 | 18.0% |
| 1.00 | | 100.0% |

Paste Formulation

| grams | material | wt % |
|---|---|---|
| 5 | ITO powder Exp #5 | 80.65% |
| 1 | Solvent preparation | 16.13% |
| 0.2 | Oleic acid | 3.23% |
| 6.2 | | 100.00% |

Formula for Sensor paste Experiment #5 Used in the Manufacture of 2pG Parts
Palladium Infused Indium Tin Oxide (ITO) Powder Formula from Sensor Paste Exp #11

| grams | material | wt % |
|---|---|---|
| 33 | $SnO_2$ | 88.19% |
| 3.62 | $In_2O_3$ | 9.67% |
| 0.8 | $PdCl_2$ | 2.14% |
| 37.42 | | 100.00% |

Solvent Preparation

| gram | material | wt % |
|---|---|---|
| 0.8 | Tween 20 | 12.70% |
| 4.67 | Butyl carbitol | 74.13% |
| 0.33 | Ethocellulose (Ethocel standard 10) | 5.24% |
| 0.5 | Igepal CO 630 | 7.9% |
| 6.30 | | 100.00% |

Paste Formulation

| grams | material | wt % |
|---|---|---|
| 10 | ITO powder Exp #11 | 61.35% |
| 6.3 | Solvent preparation | 38.65% |
| 16.3 | | 100.00% |

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." In this disclosure and during the prosecution of this application, means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited. In this disclosure and during the prosecution of this application, the terminology "present invention" or "invention" may be used as a reference to one or more aspect within the present disclosure. The language present invention or invention should not be improperly interpreted as an identification of criticality, should not be improperly interpreted as applying across all aspects or embodiments (i.e., it should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features. In this disclosure, the following abbreviated terminology may be employed: "e.g." which means "for example".

The invention claimed is:

The invention claimed is:

1. A composition for use in producing a gas sensitive material with high efficiency and fast response, said composition comprising:
— $SnO_2$ — nanocrystals doped with — $In_2O_3$ — and a solution of a salt of a platinum group metal, wherein said salt of a platinum group metal is a Pd salt selected from the group comprising (ethylenediamine)palladium(II) chloride $Pd(H_2NCH_2CH_2NH_2)Cl_2$, ammonium tetrachloropalladate(II) $(NH_4)_2PdCl_4$, Bis(acetonitrile)dichloropalladium(II) $PdCl_2.(CH_3CN)_2$, Bis(benzonitrile) palladium(II) chloride $(C_6H_5CN)_2PdCl_2$, (2-methylallyl)palladium(II) chloride dimer $[(C_4H_7)PdCl]_2$, and combinations thereof.

2. The composition of claim 1, further comprising at least one of a surfactant and a blowing agent.

3. A composition for use in producing a gas sensitive material with high efficiency and fast response, said composition comprising:
$SnO_2$ nanocrystals doped with $In_2O_3$ and a solution of a salt of a platinum group metal wherein said salt is $PdCl_2$ in an HCl solution.

4. The composition of claim 3, further comprising a surfactant and a blowing agent, wherein the surfactant comprises between about 8% to about 20% of the mixture by weight and the blowing agent comprises between about 3% and about 6% of the mixture by weight.

5. The composition of claim 4, wherein the surfactant comprises about 15% of the mixture by weight and the blowing agent comprises about 5% of the mixture by weight.

6. A gas sensitive material comprising $SnO_2$ nanoparticles doped with $In_2O_3$ and an oxide of a platinum group metal, wherein said $SnO_2$ nanoparticles have a specific surface greater than 10 $m^2/g$ and wherein said $SnO_2$ nanoparticles have a mean particle size of between about 5 nm and about 20 nm.

7. The gas sensitive material of claim 6, wherein said oxide of a platinum group is the reaction product of nanoparticles $SnO_2$, $In_2O_3$, and an aqueous HCl solution of a Pd salt converted to Pd oxide.

8. The gas sensitive material of claim 6, wherein said $SnO_2$ nanoparticles have a specific surface of at least about 20 $m^2/g$.

9. The gas sensitive material of claim 8, wherein said $SnO_2$ nanoparticles have a specific surface of at least about 50 $m^2/g$.

10. The gas sensitive material of claim 6, wherein said gas is hydrogen.

11. The gas sensitive material of claim 6, wherein the oxide of the platinum group metal comprises between about 2% and about 5% of the weight of the $SnO_2$ nanoparticles and the $In_2O_3$ comprises between about 3% and about 12% of the weight of the $SnO_2$ particles.

12. A method of producing a gas sensitive material comprising the steps of blending a Pd salt solution with nanometal oxide particles to enable the Pd to associate with the oxide nanoparticles, and converting said Pd salt to a dispersed Pd oxide, wherein said Pd salt solution is a solution of a palladium salt that dissolves in dilute aqueous HCl and further comprising the step of converting said palladium salt to an oxide of palladium at a temperature below about 600 deg. C., and further comprising collecting calcined particles that pass through a 100 mesh sieve.

13. The method of claim 12, wherein said Pd salt is $PdCl_2$.

14. The method of claim 12, wherein said nanometal oxide particles comprise $SnO_2$ and $In_2O_3$.

15. The method of claim 12, comprising the step of adding at least one of a surfactant and a blowing agent and forming a multi-component paste composition.

16. The method of claim 15, wherein the surfactant is stearic acid.

17. The method of claim 15, wherein the surfactant is a compound that completely decomposes to a gas product or products and is removed at an elevated temperature from the paste composition during the formation of the gas sensitive material.

18. The method of claim 17, further comprising the step of forming the oxide nanoparticles and dispersed Pd oxide into a film and heating or calcining the film to a temperature sufficient to decompose organic components that are present in the film.

19. The method of claim 15, wherein the surfactant is a carbonic acid with long carbonic chains, or a non-ionic surfactant.

20. The method of claim 15, wherein the blowing agent is selected from group comprising, ammonium carbonate, azo-compounds, and ammonium chloride.

21. The method of claim 15, wherein the blowing agent is a compound that decomposes to a gas form, and wherein said gas is at least one of $CO_2$, $NH_3$, and $N_2$.

22. The method of claim 12, wherein said Pd salt solution is a solution of a salt selected from the group comprising (ethylenediamine)palladium(II) chloride $Pd(H_2NCH_2CH_2NH_2)Cl_2$, ammonium tetrachloropalladate(II) $(NH_4)_2PdCl_4$, Bis(acetonitrile)dichloropalladium(II) $PdCl_2.(CH_3CN)_2$, Bis(benzonitrile)palladium(II) chloride $(C_6H_5CN)_2PdCl_2$, (2-methylallyl)palladium(II) chloride dimer $[(C_4H_7)PdCl]_2$, and combinations thereof.

23. The method of claim 12, wherein said Pd salt solution is a solution of $PdCl_2$, and wherein the step of converting said palladium salt to an oxide of palladium is at a temperature below about 500 deg. C.

24. The method of claim 23, wherein nanometal oxide particles comprise $SnO_2$ and $In_2O_3$.

25. The method of claim 24, wherein the $SnO_2$ nanocrystals have a specific surface of at least about 20 $m^2/g$ and wherein the $SnO_2$ nanocrystals have a specific surface of at least about 50 $m^2/g$.

26. The method of claim 24, wherein the $SnO_2$ particles have a mean particle size of between about 5 nm and about 20 nm.

27. The method of claim 12, further comprising forming a gas sensitive material, wherein the composition of the resultant gas sensitive material comprises, an oxide of the platinum group metal comprising between about 2% and about 5% of the weight of the $SnO_2$ and the $In_2O_3$ nanometal oxide particles comprising between about 3% and about 12% of the weight of the $SnO_2$ nanocrystals.

28. The method of claim 12, further comprising the step of depositing the gas sensitive material on a substrate, incorporating said gas sensitive material in a measuring circuit, and wherein said substrate is in communication with a heat source.

29. The method of claim 12, further comprising the step of applying said gas sensitive material to a substrate by spraying or silk screening.

30. The method of claim 12, further comprising producing Pd coating on the nanoparticles, said coating being on the order of an angstrom thick.

31. A gas detection device comprising a measuring circuit, said measuring surface comprising a substrate, a resistance heater bonded to said substrate and a coating, said coating comprising $SnO_2$ nanoparticles doped with $In_2O_3$ nanoparticles and Pd oxide, said Pd oxide being formed from an acidic solution of $PdCl_2$, and wherein the contact points between individual nanoparticles of $SnO_2$ and $In_2O_3$ and the associated Pd oxide are less than about 100 Å.

32. The gas detection device of claim 31, said $SnO_2$ nanocrystals having a specific surface of at least about 50 $m^2/g$, a mean particle size of between about 5 nm and about 20 nm.

33. A composition for use in producing a gas sensitive material with high efficiency and fast response, said composition comprising:
$SnO_2$ nanocrystals doped with $In_2O_3$ and a solution of a salt of a platinum group metal,
wherein said salt of a platinum group metal is a Pd salt selected from the group comprising $PdCl_2$, (ethylenediamine)palladium(II) chloride $Pd(H_2NCH_2CH_2NH_2)Cl_2$, ammonium tetrachloropalladate(II) $(NH_4)_2PdCl_4$, Bis(acetonitrile)dichloropalladium(II) $PdCl_2.(CH_3CN)_2$, Bis(benzonitrile)palladium(II) chloride $(C_6H_5CN)_2PdCl_2$, (2-methylallyl)palladium(II) chloride dimer $[(C_4H_7)PdCl]_2$, and combinations thereof,
wherein said salt of Pd is $PdCl_2$ in an aqueous solution,
further comprising a surfactant and a blowing agent, and
wherein the surfactant comprises between about 8% to about 20% of the mixture by weight and the blowing agent comprises between about 3% and about 6% of the mixture by weight.

34. The composition of claim 33, wherein the surfactant comprises about 15% of the mixture by weight and the blowing agent comprises about 5% of the mixture by weight.

35. A gas sensitive material comprising $SnO_2$ nanoparticles doped with $In_2O_3$ and an oxide of a platinum group metal, wherein said $SnO_2$ particles have a specific surface greater than 10 $m^2/g$, wherein the contact points between individual nanoparticles of $SnO_2$ and $In_2O_3$, and the associated Pd oxide are less than about 100 Å.

36. A method of producing a gas sensitive material comprising the steps of blending a Pd salt solution with nanometal oxide particles to enable the Pd to associate with the oxide nanoparticles, and converting said Pd salt to a dispersed Pd oxide, further comprising the step of adding a surfactant and processing to produce a gas sensitive material having a molecular spacing of up to about 100 Å between the contacting nanoparticles.

37. A method of producing a gas sensitive material comprising the steps of blending a Pd salt solution with nanometal oxide particles to enable the Pd to associate with the oxide nanoparticles, and converting said Pd salt to a dispersed Pd oxide:

wherein said Pd salt solution is a solution of a palladium salt that readily dissolves in dilute aqueous HCl and further comprising the step of converting said palladium salt to an oxide of palladium at a temperature below about 600 deg. C., without leaving significant residues;

wherein nanometal oxide powders comprise $SnO_2$ and $In_2O_3$;

wherein the step of blending a Pd salt solution with the nanometal oxide powders comprises coating or impregnating said $SnO_2$ and $In_2O_3$ nanopowders with $PdCl_2$, and then calcining to remove any remaining chlorine components;

wherein said calcining is at a calcining temperature below about 500 deg. C. and further comprising collecting calcined powders that can pass through a 100 mesh sieve.

38. A method of producing a gas sensitive material comprising the steps of:

blending a Pd salt solution with nanometal oxide particles to enable the Pd to associate with the oxide nanoparticles, and converting said Pd salt to a dispersed Pd oxide;

adding a surfactant and forming a multi-component paste composition, said step of adding surfactant being prior to the step of calcining;

removing said surfactant in the calcining step, leaving the contact distances necessary to increase the number and efficacy of the active centers;

and wherein a Pd coating is produced on the nanoparticles, said coating being on the order of an angstrom thick.

39. A method of producing a gas sensitive material comprising the steps of blending a Pd salt solution with nanometal oxide particles to enable the Pd to associate with the oxide nanoparticles, and converting said Pd salt to a dispersed Pd oxide;

the step of adding a surfactant and a blowing agent and forming a multi-component paste composition, said step of adding a surfactant being prior to calcining;

removing said surfactant in the calcining step, leaving the contact distances necessary to increase the number and efficacy of the active centers;

wherein said nanometal oxide particles comprise $SnO_2$ and $In_2O_3$ and the surfactant comprises between about 8% to about 20% of the $SnO_2$, $In_2O_3$, $PdCl_2$ mixture by weight and the blowing agent comprises between about 3% and about 6% of the mixture by weight.

40. The method of claim 39, wherein the blowing agent is selected from group comprising, ammonium carbonate, azo-compounds, and ammonium chloride.

41. The method of claim 39, wherein the blowing agent is a compound that decomposes to a gas form, and wherein said gas is at least one of $CO_2$, $NH_3$, and $N_2$.

42. A gas detection device comprising a measuring circuit, said measuring circuit comprising a substrate, a resistance heater bonded to said substrate and a coating, said coating comprising $SnO_2$ nanoparticles doped with $In_2O_3$ nanoparticles and Pd oxide, said Pd oxide being formed from a solution of $PdCl_2$, said $SnO_2$ nanocrystals having a specific surface of at least about 50 $m^2/g$, a mean particle size of between about 5 nm and about 20 nm, and the contact points between individual nanoparticles of $SnO_2$ and $In_2O_3$ and the associated Pd oxide are less than about 100 Å.

* * * * *